(12) United States Patent
Smith et al.

(10) Patent No.: US 8,007,473 B2
(45) Date of Patent: Aug. 30, 2011

(54) ACCESS ASSEMBLY WITH MULTI-FLAPPER DESIGN

(75) Inventors: Robert C. Smith, Middletown, CT (US); Ernest Aranyi, Easton, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 209 days.

(21) Appl. No.: 12/403,647

(22) Filed: Mar. 13, 2009

(65) Prior Publication Data

US 2009/0259186 A1 Oct. 15, 2009

Related U.S. Application Data

(60) Provisional application No. 61/043,814, filed on Apr. 10, 2008.

(51) Int. Cl.
*A61M 5/178* (2006.01)
(52) U.S. Cl. .................................. 604/167.04
(58) Field of Classification Search ............ 604/167.01, 604/167.02, 167.03, 167.04, 167.05, 167.06
See application file for complete search history.

(56) References Cited

U.S. PATENT DOCUMENTS

| | | | |
|---|---|---|---|
| 5,104,383 A * | 4/1992 | Shichman | 604/167.06 |
| 5,209,737 A | 5/1993 | Ritchart et al. | |
| 5,211,633 A | 5/1993 | Stouder, Jr. | |
| 5,342,315 A * | 8/1994 | Rowe et al. | 604/167.06 |
| 5,496,280 A * | 3/1996 | Vandenbroek et al. | 604/167.03 |
| 5,569,205 A | 10/1996 | Hart et al. | |
| 5,730,728 A * | 3/1998 | Hoskin et al. | 604/185 |
| 5,820,600 A | 10/1998 | Carlson et al. | |
| 6,228,061 B1 | 5/2001 | Flatland et al. | |
| 6,551,270 B1 | 4/2003 | Bimbo et al. | |
| 7,438,702 B2 | 10/2008 | Hart et al. | |

FOREIGN PATENT DOCUMENTS

| | | |
|---|---|---|
| DE | 297 17 940 | 1/1998 |
| GB | 2 284 452 | 7/1995 |
| GB | 2298906 | 9/1996 |

OTHER PUBLICATIONS

European Search Report, Application No. EP 09251066.8 dated Jul. 13, 2009.

* cited by examiner

*Primary Examiner* — Nicholas D Lucchesi
*Assistant Examiner* — Aarti B Berdichevsky

(57) ABSTRACT

An apparatus for the reception of an instrument inserted through a surgical portal apparatus includes a valve mount, a major opening through the valve mount, a primary valve for selectively sealing the major opening, a minor opening through the primary valve, and a secondary valve for selectively sealing the minor opening. Components of both the major valve and the minor valve may be displaced to permit passage of a broad instrument, while components of only the secondary valve may be displaced to permit passage of a narrow instrument.

15 Claims, 18 Drawing Sheets

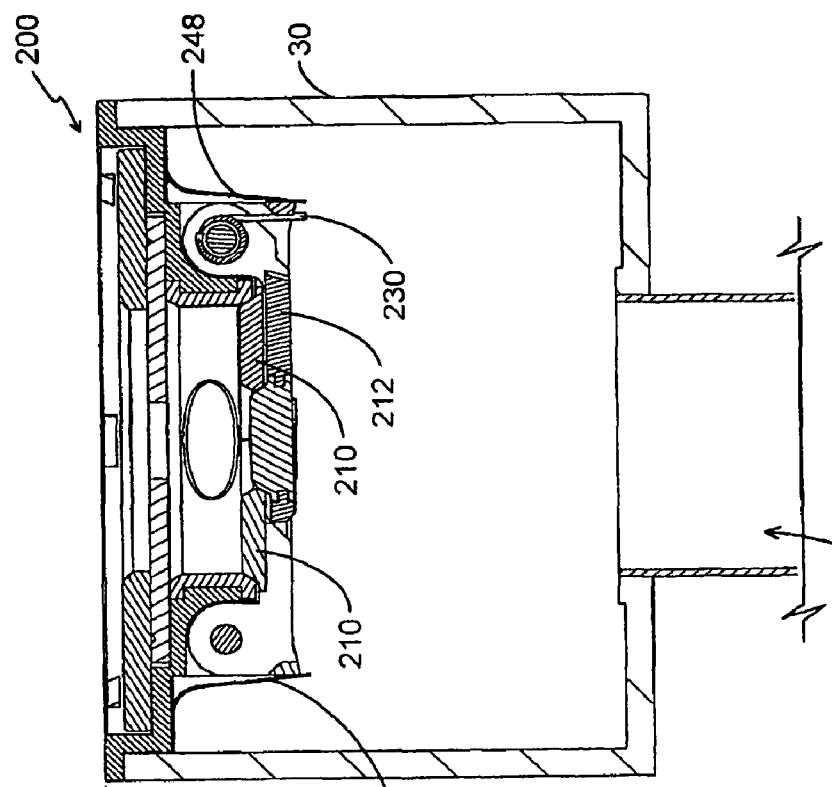
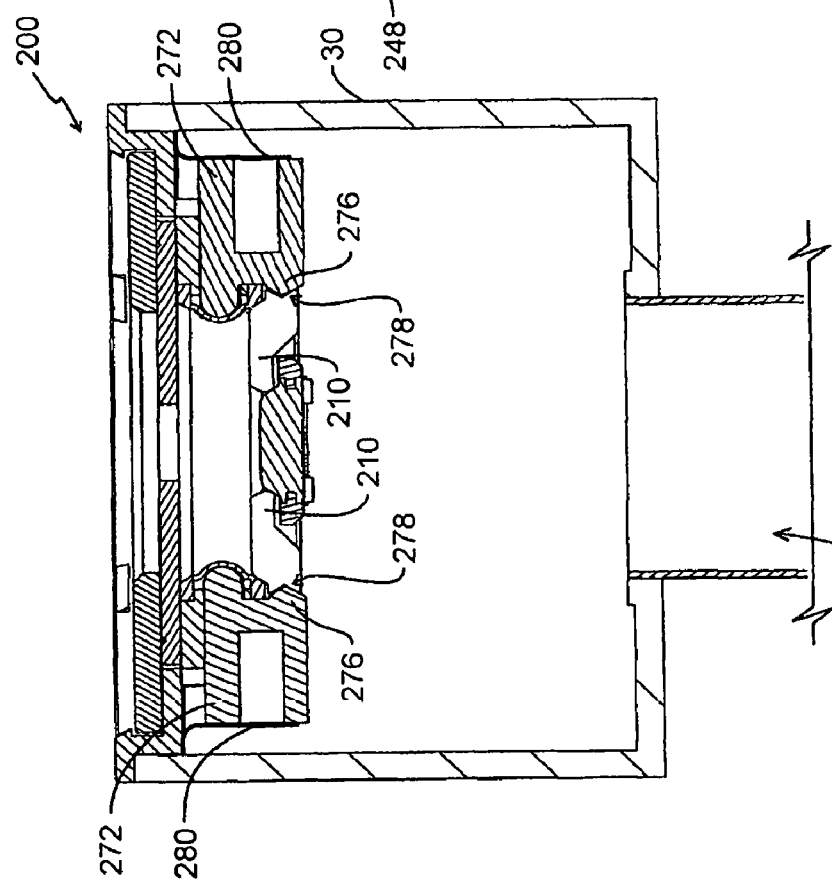

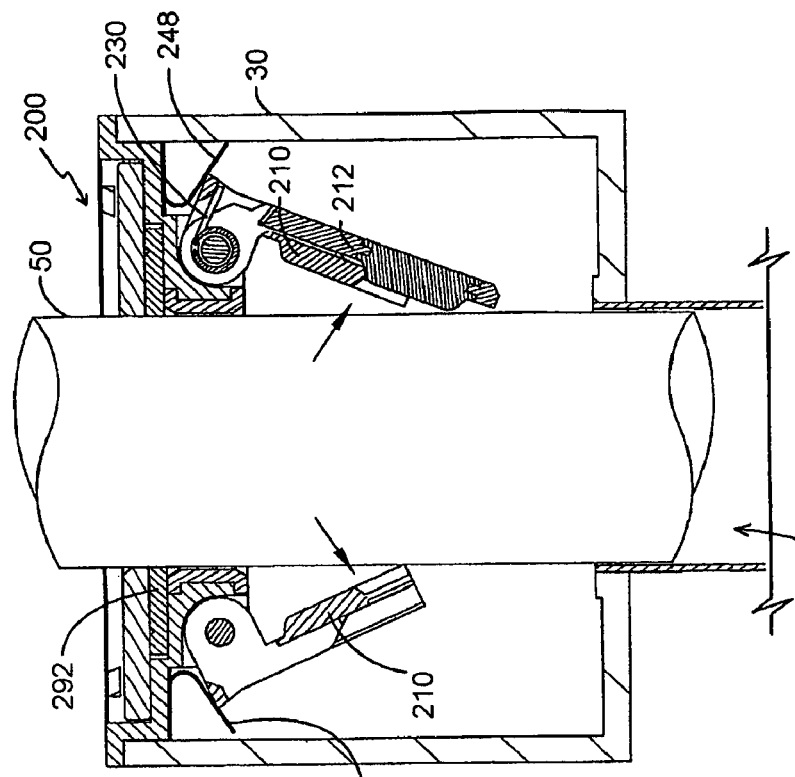
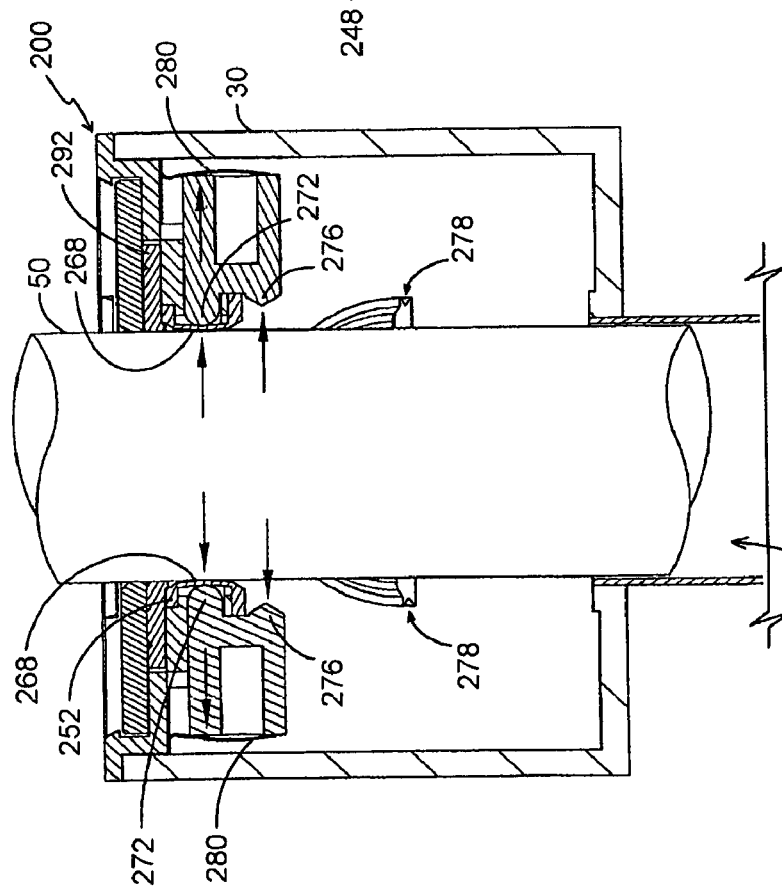

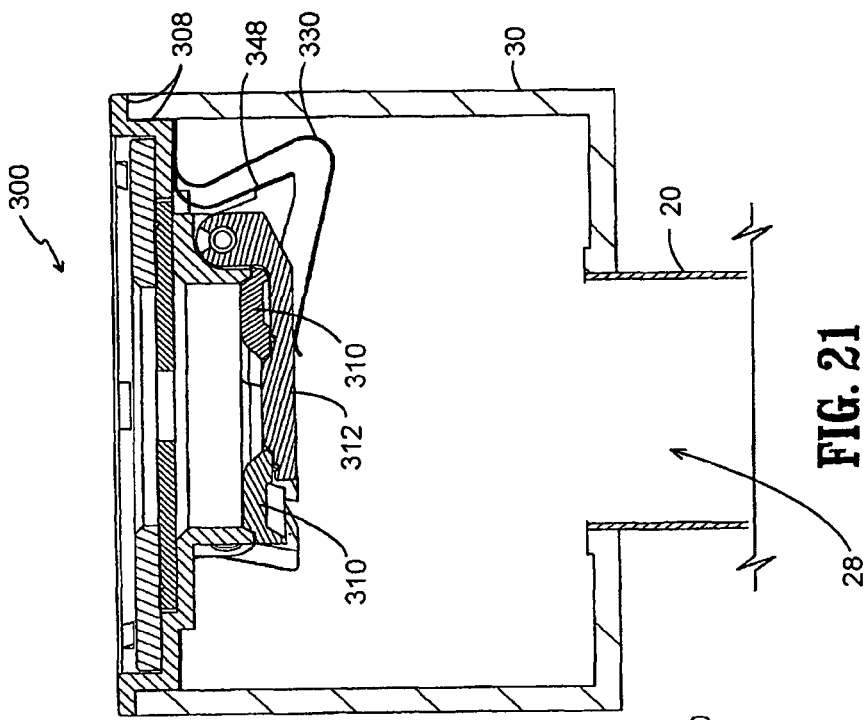
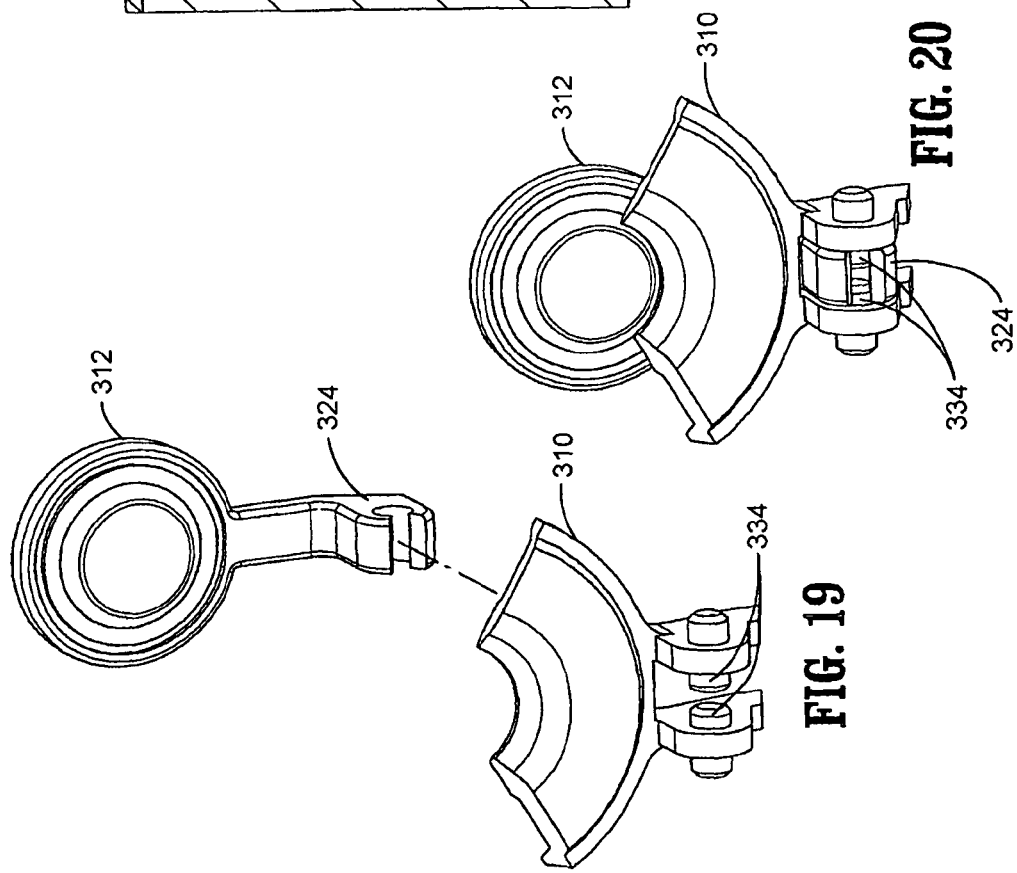
FIG. 19
FIG. 20
FIG. 21

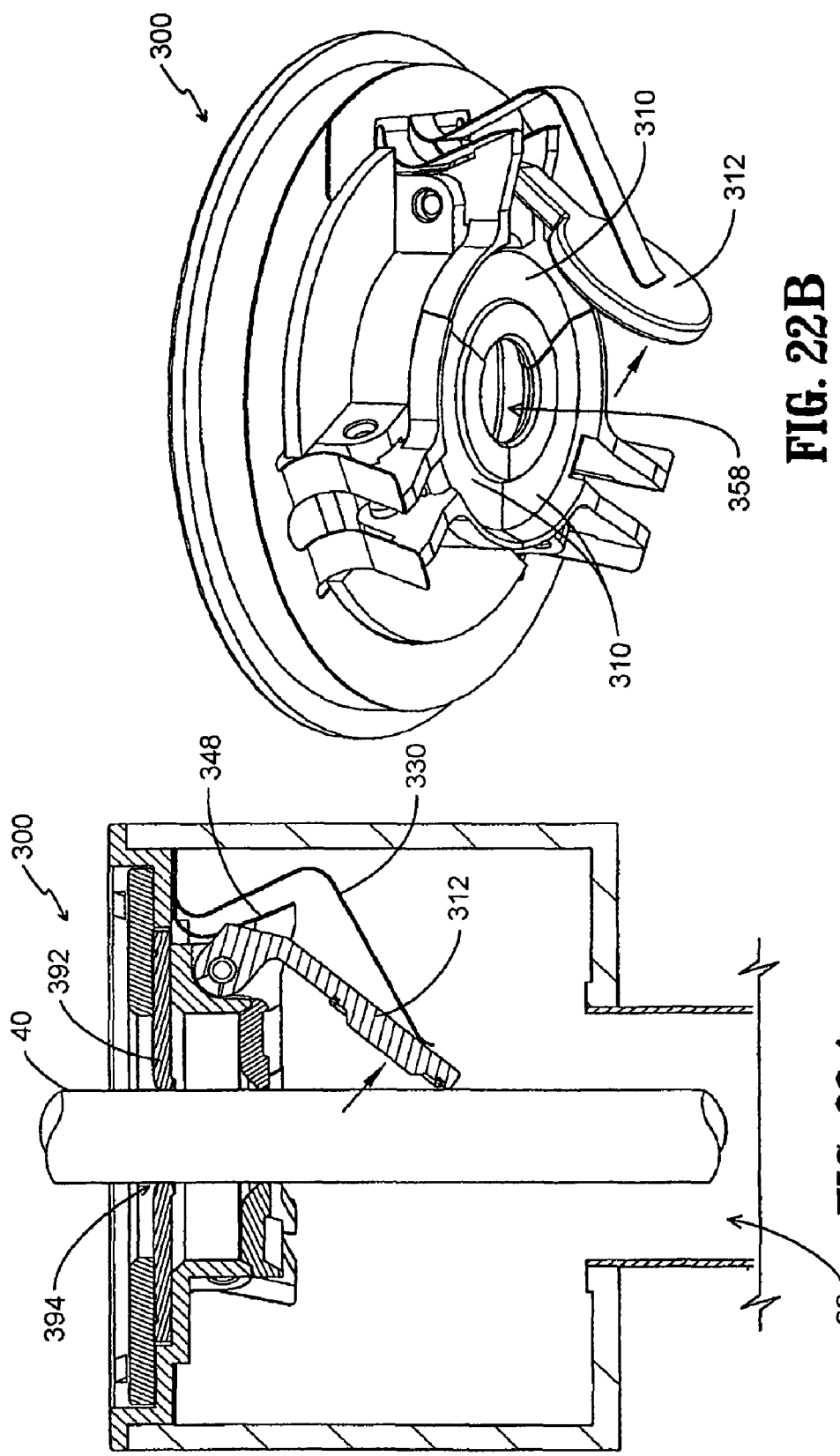

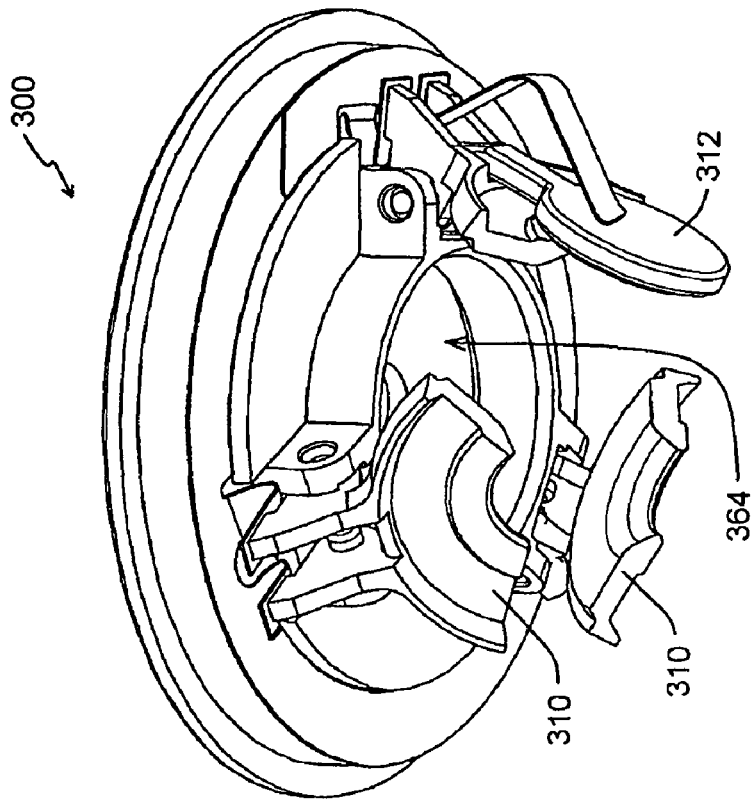
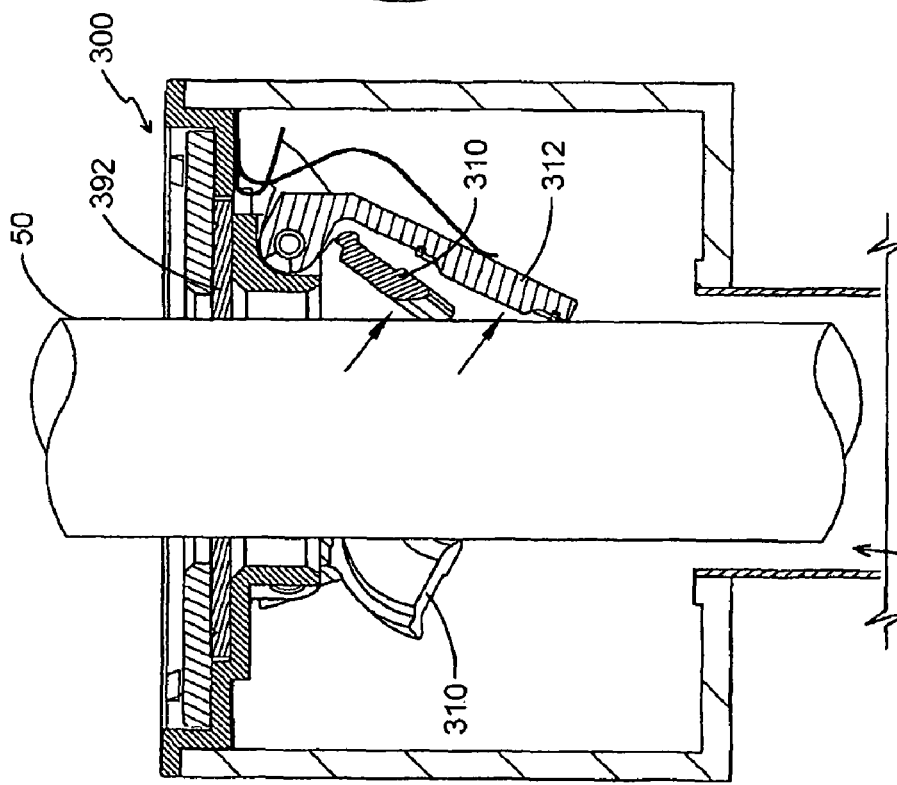
FIG. 23B
FIG. 23A

ACCESS ASSEMBLY WITH MULTI-FLAPPER DESIGN

CROSS REFERENCE TO RELATED APPLICATION

The present application claims the benefit of and priority to U.S. Provisional Application Ser. No. 61/043,814 filed on Apr. 10, 2008, the entire contents of which are incorporated herein by reference.

BACKGROUND

1. Technical Field

The present disclosure relates generally to a surgical portal apparatus employing a system for maintaining a fluid-tight seal across a passageway for surgical instruments. In particular, the disclosure relates to a surgical portal apparatus employing a multiple flapper valve mechanism as part of a seal system.

2. Background of Related Art

Surgical procedures such as laparoscopic, arthroscopic, and endoscopic procedures in general are termed minimally invasive at least in part because the incision required is relatively small, perhaps one inch in length or less. Small incisions are preferred because they are inherently less traumatic to the surrounding body tissue. Also, small incisions subject internal organs to a limited exposure to the contaminants in the outside atmosphere. Thus, small incisions enable shorter hospital stays and faster recoveries with less pain and scarring than is common with the larger incisions required for conventional surgery.

Endoscopic surgery is possible due in part to the availability of instruments designed specifically for this purpose. A cannula, for example, is an elongated tube, typically 5 mm to 13 mm in diameter, which may be configured to have a distal end inserted through the small incision to provide a working conduit to an internal body cavity adjacent an operative site. The body cavity is often inflated with an insufflation gas, carbon dioxide for example, to separate the body wall from vital organs. This provides a space where a surgeon may introduce viewing equipment or maneuver tools into position without damaging surrounding tissue. Various other instruments may then be inserted and withdrawn through the cannula for access to the working space and operative site. In order to fit through a cannula and enable a surgeon to manipulate tissue far removed from the incision, instruments adapted for endoscopic surgery typically include a long and narrow cylindrical shaft. The exact size and shape of the instrument shaft, however, may vary for the many instruments required for a single procedure.

Endoscopic procedures generally require that any instrumentation inserted into the patient's body be sealed, i.e. provisions must be made to ensure insufflation gasses, blood and other fluids do not escape the body through the cannula. Furthermore, a seal acts to prevent contamination of the body cavity by the outside environment. In the absence of such a fluid-tight seal, many of the attendant advantages of minimally invasive surgery are lost.

In a typical procedure, a surgeon may need to install a converter to the cannula to ensure a fluid-tight seal is maintained each time a new instrument having a differing diameter is needed. This process can be cumbersome for the surgeon and increase the time a patient must be subjected to the surgery. Accordingly, a need exists for a cannula seal assembly capable of accommodating variously sized instruments while maintaining a fluid-tight seal across the cannula.

SUMMARY

The present disclosure describes a surgical portal apparatus which permits a surgical instrument to access a tissue site while maintaining a seal about the instrument. The portal apparatus includes a portal member dimensioned for positioning within body tissue and defining a longitudinal axis. A passageway through the portal member provides access to the tissue site for an instrument. A valve mount defines a major opening in communication with the passageway, and a primary valve is mounted to the valve mount. The primary valve is adapted to move between a first position to substantially seal the major opening and a second position displaced from the major opening to permit passage of a relatively broad surgical instrument through the major opening. The primary valve defines a minor opening dimensioned to receive a relatively narrow instrument. A secondary valve mounted to the portal member is adapted to move relative to the primary valve between an initial position to substantially seal the minor opening and an actuated position displaced from the minor opening to permit passage of the marrow instrument.

At least one of the primary valve and secondary valve may be adapted for pivotal movement about an axis transverse to the longitudinal axis. A housing may be coupled to a proximal end of the portal member and the valve mount may be coupled to the housing. A lock member may be included to prevent the major valve from opening upon introduction of the narrow instrument. The lock member may include a disengagement surface adapted to cause the lock member to be displaced upon engaging the broad instrument to permit opening of the major valve.

The primary valve may be radially segmented such that a plurality of segments are disposed about the major opening, and each segment may be mounted pivotally about an independent axis. The major valve may be bifurcated to include two segments or trifurcated to include three segments. A septum seal may be disposed proximally with respect to the major valve for engaging an instrument and forming a seal therewith. The primary valve and the secondary valve may be normally biased to their respective first and initial positions to maintain a fluid-tight seal across the passageway in the absence of an instrument.

In another aspect of the disclosure, a cannula seal includes a valve mount for mounting the cannula seal across a passageway through a cannula defining a longitudinal axis. A radially segmented primary valve is included for sealing a major opening through the body. Each segment is mounted pivotally to be moveable to move the primary valve between a first position and a second position. When in the first position, the primary valve defines a minor opening therethrough. A secondary valve is included for selectively sealing the minor opening. The secondary valve is coupled to at least one of the segments such that the secondary valve is displaced when the segment to which it is coupled when the primary valve is moved between first and second positions.

The secondary valve may be pivotally mounted to pivot about the same axis about which the segment to which it is coupled pivots. A biasing member may be included for biasing the secondary valve to an initial position to seal the minor opening. A lock member may be included to prevent the plurality of segments from pivoting upon introduction of a narrow instrument. The lock member may include a disengagement surface adapted to cause the lock member to be displaced upon engaging a broad instrument to permit the plurality of segments to pivot. A septum seal may be disposed proximally with respect to the primary valve for engaging and forming a seal with an instrument.

In another aspect of the disclosure, a surgical portal apparatus for permitting access to a tissue site includes a portal member for positioning within body tissue and defining a longitudinal axis. The portal member has a longitudinal passageway providing access to a tissue site and includes a valve mount defining a major opening in communication with the longitudinal passageway. A primary valve is mounted to the portal member and is adapted to move between a first position to substantially seal the major opening, and a second position displaced from the major opening. The primary valve defines a minor opening having an internal dimension less than a corresponding internal dimension of the major opening. A secondary valve mounted to the portal member is adapted to move relative to the primary valve between an initial position to substantially seal the minor opening and an actuated position displaced from the minor opening.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 12 is a cross-sectional view of the seal assembly taken along line 12-12 of FIG. 10 inserted into a housing;

FIG. 13 is a view similar to FIG. 12 viewed from an orthogonal direction;

FIG. 15A is a view similar to FIG. 14A depicting a broad instrument introduced into the proximal end of the portal apparatus;

FIG. 15B is a perspective view of a distal side of the seal assembly of FIG. 9 depicting the bifurcated major valve in an open configuration;

FIG. 19 is a perspective view with parts separated of the minor flapper and a single radial segment of major flapper of FIG. 18;

FIG. 20 is a perspective view with parts assembled of the minor flapper and a single radial segment of major flapper;

FIG. 21 is a cross-sectional view of the seal assembly taken along line 21-21 of FIG. 16 inserted into a housing;

FIG. 22A is a view similar to FIG. 21 depicting a narrow instrument introduced into the proximal end of the portal apparatus;

FIG. 22B is a perspective view of a distal side of the seal assembly of FIG. 9 depicting the minor valve in an open configuration;

FIG. 23A is a view similar to FIG. 22A depicting a broad instrument introduced into the proximal end of the portal apparatus; and FIG. 23B is a perspective view of a distal side of the seal assembly of FIG. 9 depicting the radially segmented major valve in an open configuration.

DETAILED DESCRIPTION OF PREFERRED EMBODIMENTS

Figures 1, 2:
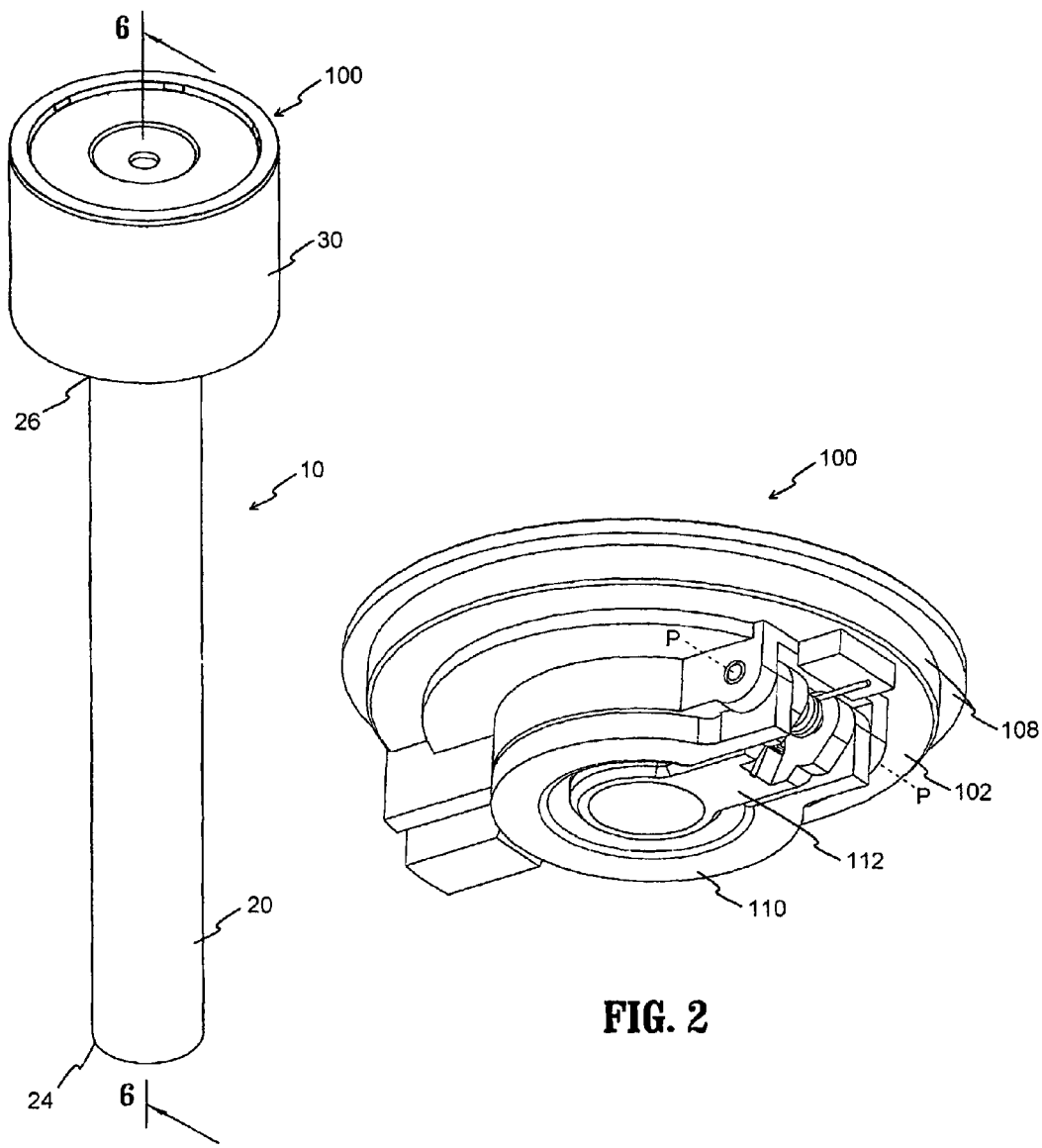
FIG. 1 is a perspective view of a surgical portal apparatus in accordance with the present disclosure.
FIG. 2 is a perspective view of a distal side of a first embodiment of a multi-flapper seal assembly having a dual flapper configuration in accordance with the present disclosure.

The present disclosure contemplates the introduction into a person's body of all types of surgical instruments including clip appliers, graspers, dissectors, retractors, staplers, laser fibers, photographic devices, endoscopes and laparoscopes, tubes, and the like. All such objects are referred to herein generally as "instruments." In the drawings and in the description which follows, the term "proximal," as is traditional, will refer to the direction toward the operator or a relative position on the surgical device or instrument which is closer to the operator, while the term "distal" will refer to the direction away from the operator or relative position of the instrument which is further from the operator.

Referring initially to FIGS. 1 through 8B, a first embodiment of the disclosure includes an embedded flapper seal system. As seen in FIG. 1, a surgical portal apparatus 10 includes a portal member such as cannula 20, which is adapted to be positioned adjacent a surgical site. Cannula 20 is formed as an elongate hollow sleeve open at both a distal end 24 and at the opposite proximal end 26, and defines a longitudinal axis "A" (FIG. 5) extending through surgical portal apparatus 10. A longitudinal passageway 28 (FIG. 6A)

extends through the interior of cannula 20 and permits passage of an elongated object therethrough. Cannula 20 may be formed from a medical grade material such as stainless steel, plastic or other rigid materials.

Housing 30 is rigidly coupled to the proximal end 26 of cannula 20. The interior of housing 30 is open and permits the introduction of elongated objects such as relatively narrow instrument 40 (FIG. 7) and relatively broad instrument 50 (FIG. 8). Housing 30 also permits the mounting and operation of dual-flapper seal assembly 100 therein. With dual flapper assembly seal assembly 100 in place, an insufflation pressure may be maintained at the surgical site and throughout portal apparatus 10. A port (not shown) may be provided through the housing for introducing additional insufflation gas into the body cavity.

Figure 3:
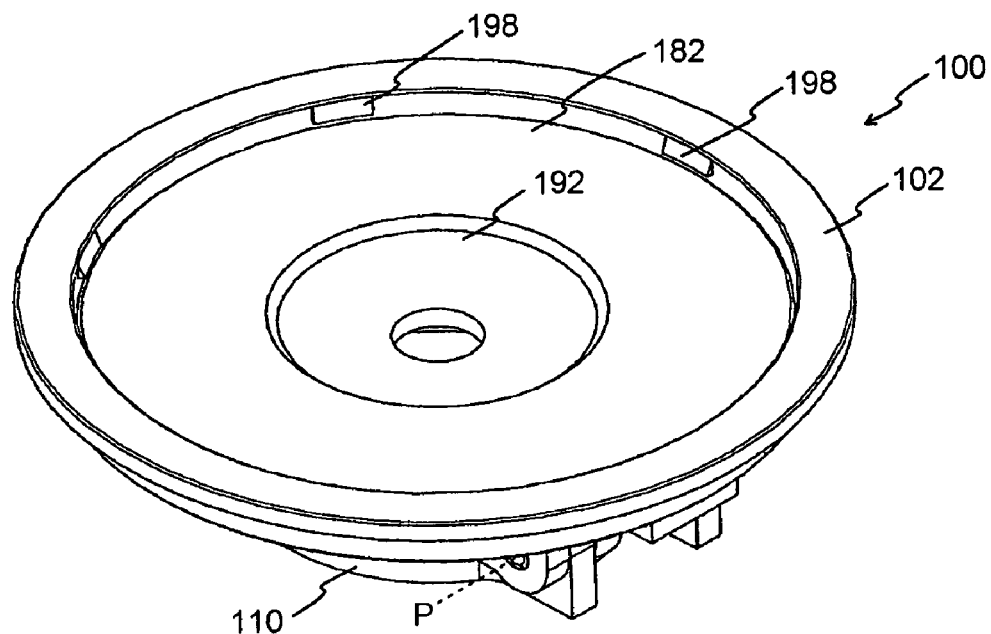
FIG. 3 is perspective view of a proximal side of the seal assembly of FIG. 2.
Figure 4:
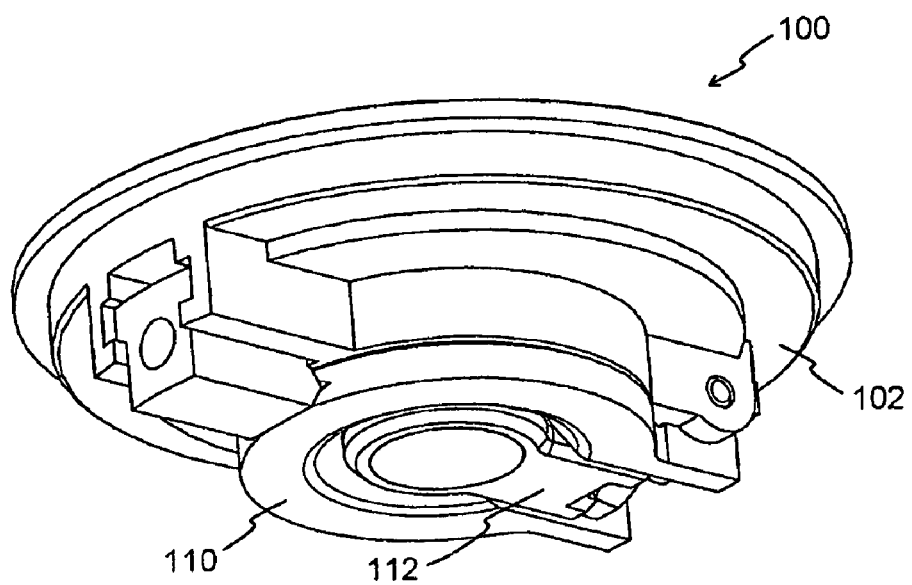
FIG. 4 is a reverse angle perspective view of the seal assembly of FIG. 2.

Referring now to FIGS. 2 through 4, dual flapper seal assembly 100 generally includes a body 102 having mounting surfaces 108 for interfacing with the housing 30 in a substantially fluid tight manner. Body 102 defines a valve mount that may be formed as separate component as depicted in FIG. 2, or may be formed integrally with housing 30, cannula 20 or any other appropriate component of surgical portal apparatus 10. A primary valve includes major flapper 110, which, when in a first position, abuts a portion of body 102 to form a fluid-tight interface therewith. A secondary valve includes minor flapper 112, which, when in an initial position abuts a portion of major flapper 110 to form fluid-tight interface therewith. Major flapper 110 and minor flapper 112 are both mounted pivotally with respect to an axis "P," which is transverse to a longitudinal axis of the cannula 20. Together, major flapper 110 and minor flapper 112 serve to seal passageway 28 in the absence of an instrument. As described in greater detail below, minor flapper 112 may pivot about axis "P" to move to an actuated position to permit passage of a narrow instrument 40, while major flapper 110 and minor flapper 112 may both pivot together about axis "P" to move major flapper 110 to a second position to permit passage of a broad instrument 50.

Figure 5:
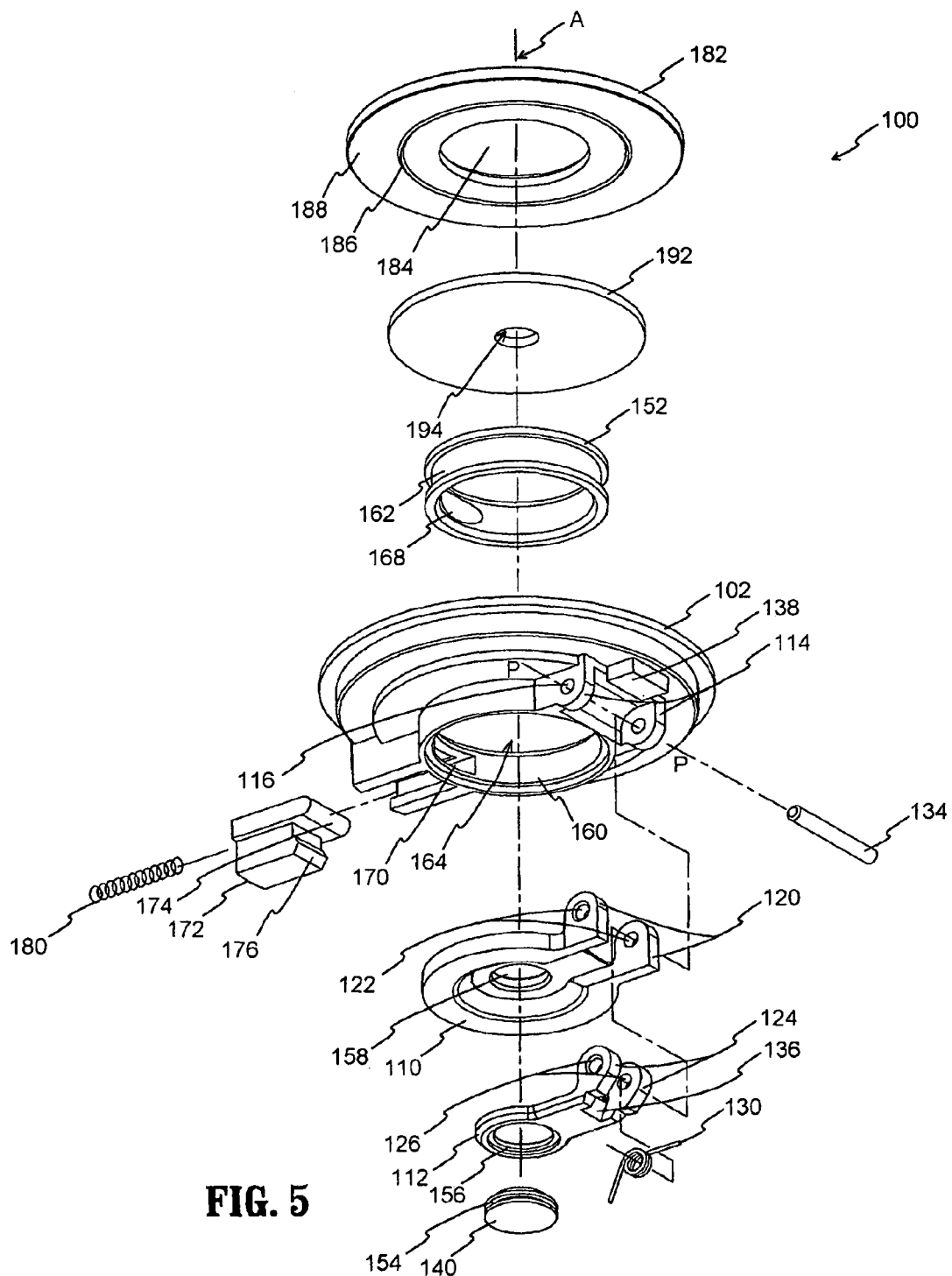
FIG. 5 is a perspective view with parts separated of the seal assembly of FIG. 2.

Referring now to FIG. 5, the assembly and construction of dual-flapper seal assembly 100 is described. Body 102 includes a pair of hanging body brackets 114 each with a bore 116 along a pivot axis "P." Body brackets 114 are spaced to receive major brackets 120 extending proximally from major flapper 110, such that holes 122 through major brackets 120 are aligned with bores 116 along axis "P." Likewise, major brackets 120 are spaced to receive minor brackets 124 extending proximally from minor flapper 112, such that holes 126 through minor brackets 124 are align with holes 122 along axis "P." Finally, minor brackets 124 are spaced to receive torsion spring 130 between them, such that torsion spring 130 is aligned with axis "P." Pivot pin 134 is inserted through bores 116, holes 122, 126 and torsion spring 130. Pivot pin 134 may be press fit within bores 116 or attached to body by other means to secure major flapper 110, minor flapper 112 and torsion spring 130. Holes 122, 126 however are sized to allow major flapper and minor flapper to pivot about axis "P."

Torsion spring 130 exerts pressure against surface 136 on minor flapper 112 and surface 138 on body 102 and thus acts as a biasing member to maintain major flapper 110 and minor flapper 112 in a closed condition. The pressure exerted by torsion spring 130 may also serve to compress elastomeric plug 140 and elastomeric liner 152 to create two separate flapper seals. First, a minor flapper seal is formed by elastomeric plug 140 when minor flapper 112 is in its initial position. Elastomeric plug 140 is captured within minor flapper 112 by the interface of annular notch 154 in the elastomeric plug 140 with annular rim 156 provided on an inner surface of minor flapper 112. Thus, elastomeric plug 140 moves along with minor flapper 112 and the closure bias imparted to minor flapper 112 may serve to compress elastomeric plug about minor opening 158 in major flapper 110 to create a seal about minor opening 158. Secondly, elastomeric liner 152 may be compressed to form a major flapper seal. Elastomeric liner 152 is captured within body 102 by the interface of annular protrusion 160 provided on body 102 with annular channel 162 of elastomeric liner 142, and thus remains stationary within body 102. In its normally biased closed condition of its first position, major flapper 110 abuts elastomeric liner 152 such that a seal is formed about a major opening 164 through body 102. Both major flapper 110 and minor flapper 112 are thus biased into sealing abutment with a corresponding surface fully closing opening 164 through body 102.

A reduced thickness dimple 168 in elastomeric liner 152 may be aligned with lateral opening 170 through body 102. Lateral opening 170 slidingly accepts a lock member 172 such that rounded disengagement head 174 protrudes against dimple 168. Lock member 172 includes a catch 176 that interfaces with a notch 178 (best seen in FIG. 8B) in major flapper 110. Compression spring 180 is positioned between lock member 172 and an interior wall of housing 30 such that lock member 172 is biased radially inward (see, e.g. FIG. 6A).

At the proximal end of dual flapper seal assembly 100, a cover plate 182 includes a central opening 184 and an annular ridge 186 protruding from a distal face 188. Annular ridge 186 is pointed in cross section such that it may dig into and deform a portion of septum seal 192 to secure its relative position against distal face 188. Septum seal 192 is a relatively flat member formed from a low durometer polymer making it particularly adaptable and deformable. Extending through a central portion of septum seal 192 is an orifice 194, which is capable of expanding to accommodate instruments of various sizes. Septum seal 192 is held in place between body 102 and cover plate 182 by a radial array of flaps 198 (best seen in FIG. 3) protruding inwardly from body 102.

Figure 6A:
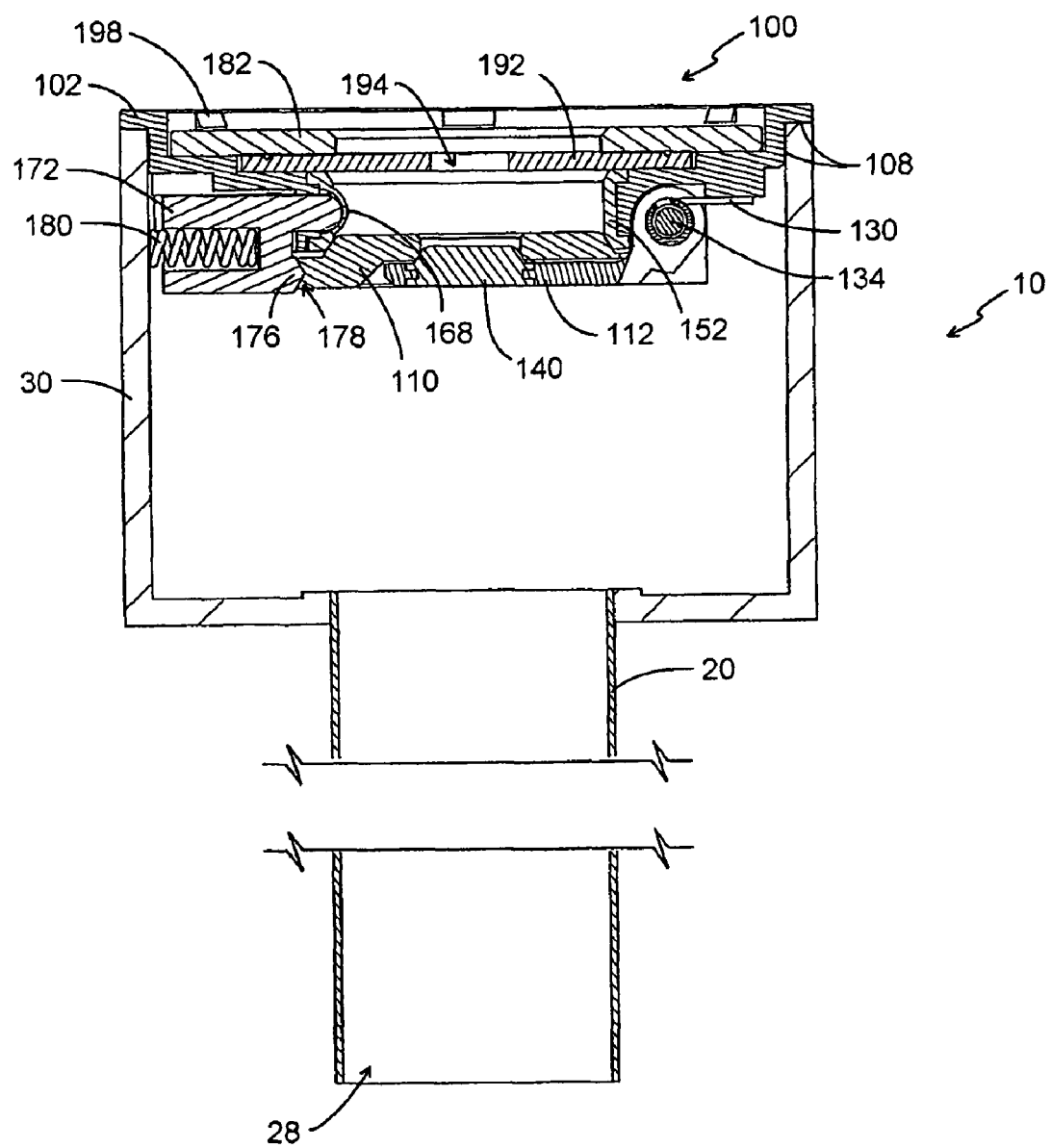
FIG. 6A is a cross-sectional view of the portal apparatus taken along line 6-6 of FIG. 1.
Figure 6B:
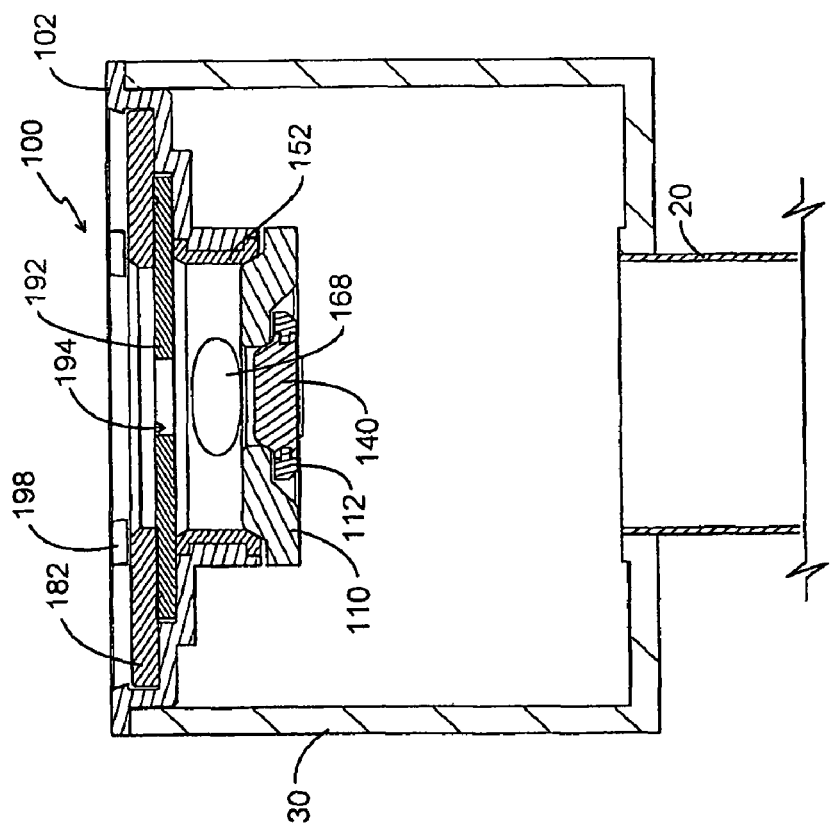
FIG. 6B is a cross-sectional view of a proximal portion of the portal apparatus of FIG. 1 having a view angle orthogonal to the view angle of FIG. 6A.

Referring now to FIGS. 6A and 6B, dual-flapper seal assembly 100 is depicted in place within housing 30 in a normally biased condition. A fluid tight connection between the mounting surfaces 108 of body 102 and housing 30 may be made by a friction fit, ultrasonic welding, adhesive or other appropriate means. Although orifice 194 in septum seal 192 remains open, passageway 28 is sealed by the fluid tight interfaces formed by elastomeric liner 152 and elastomeric plug 140 as described above.

Figure 7A:
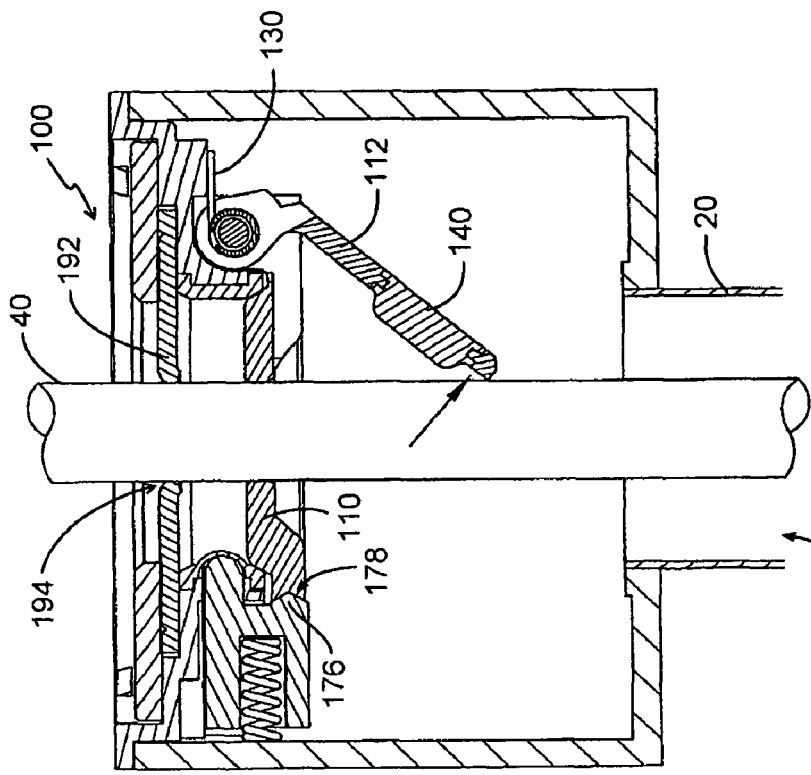
FIG. 7A is a view similar to FIG. 6A depicting a narrow instrument introduced into the proximal end of the portal apparatus.

Referring to FIG. 7A, the use of dual-flapper seal assembly 100 with narrow instrument 40 is described. Narrow instrument 40 may be inserted on a distal direction from the proximal end where it first encounters septum seal 192. To accommodate the shaft of narrow instrument 40, septum seal 192 deforms to expand central orifice 194. This deformation creates a fluid-tight interface about the shaft of instrument 40. As it travels distally past septum seal 192, narrow instrument 40 next encounters elastomeric plug 140 and tends to act against the bias of torsion spring 130 to open minor flapper 112, moving it to its actuated position as shown. With minor flapper 112 open to its actuated position, the bias provided by torsion spring 130 is not transmitted to major flapper 110. However, gravity or incidental contact between narrow instrument 40 and major flapper 110 will not tend to open major flapper 110 due to the engagement of the catch 176 of lock member 172 with the notch 178 on major flapper 110. Because major flapper 110 remains closed in its first position, it may assist in centering narrow instrument 40 within the passageway 28.

Figure 7B:
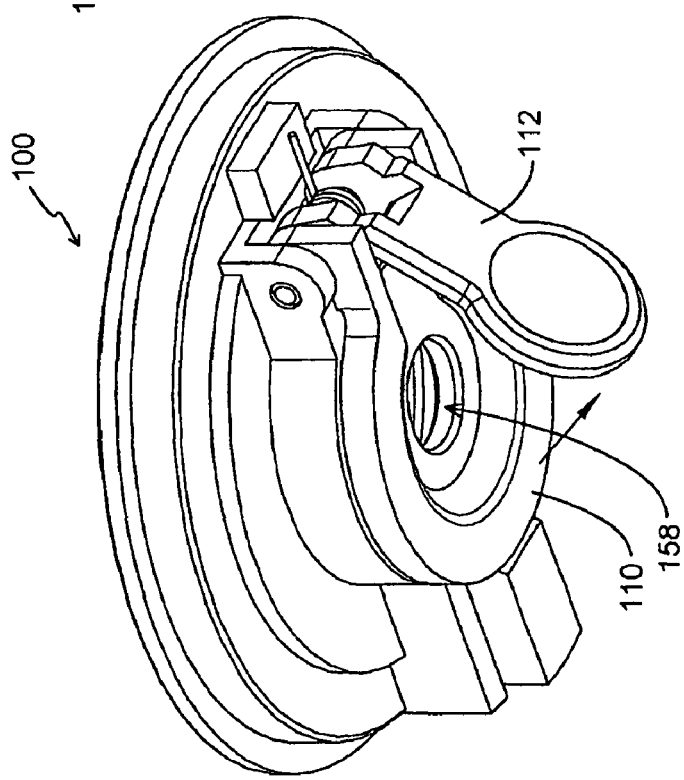
FIG. 7B is a perspective view of a distal side of the seal assembly of FIG. 2 depicting the minor valve in an open configuration.

With the minor flapper 112 open to its actuated position, the seal through the passageway 28 depends on the interface between the septum seal 192 and the shaft of instrument 40 while narrow instrument 40 is in use. When the use of narrow instrument 40 is complete, narrow instrument 40 may be withdrawn in a proximal direction. Minor flapper 112 is returned to its initial position and normally closed condition under the bias of torsion spring 130 before the seal about the instrument shaft is compromised. In this way a seal across the passageway 28 may be maintained at all times, i.e. before, during and after insertion, use and withdrawal of instrument 40. FIG. 7B depicts dual flapper seal assembly 100 with minor flapper 112 open it its actuated position revealing the minor opening 158 through major flapper 110.

Figure 8A:
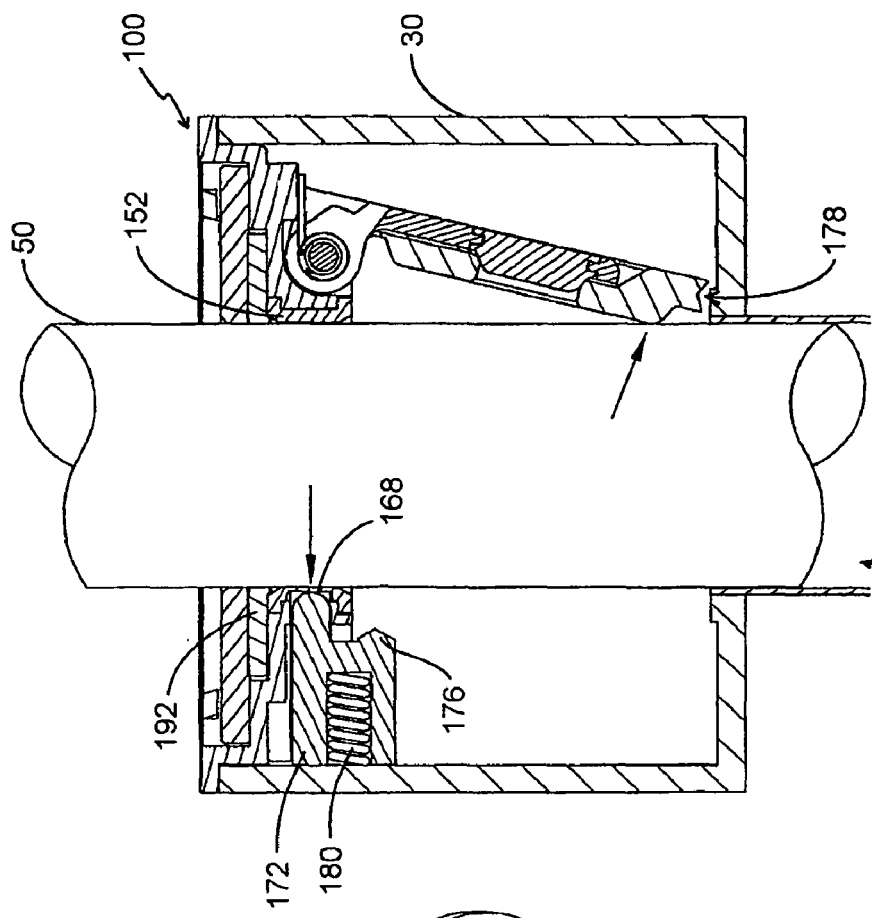
FIG. 8A is a view similar to FIG. 7A depicting a broad instrument introduced into the proximal end of the portal apparatus.
Figure 8B:
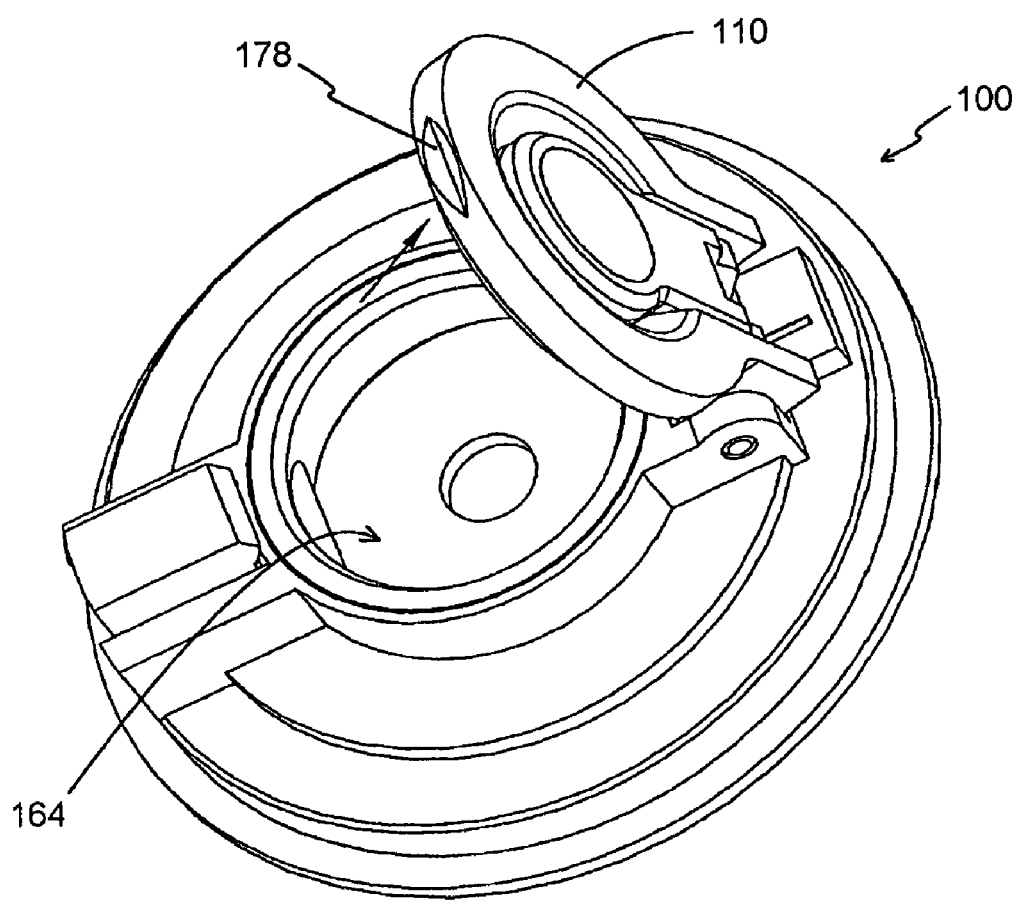
FIG. 8B is a perspective view of a distal side of the seal assembly of FIG. 2 depicting the major valve in an open configuration.
Figure 10:
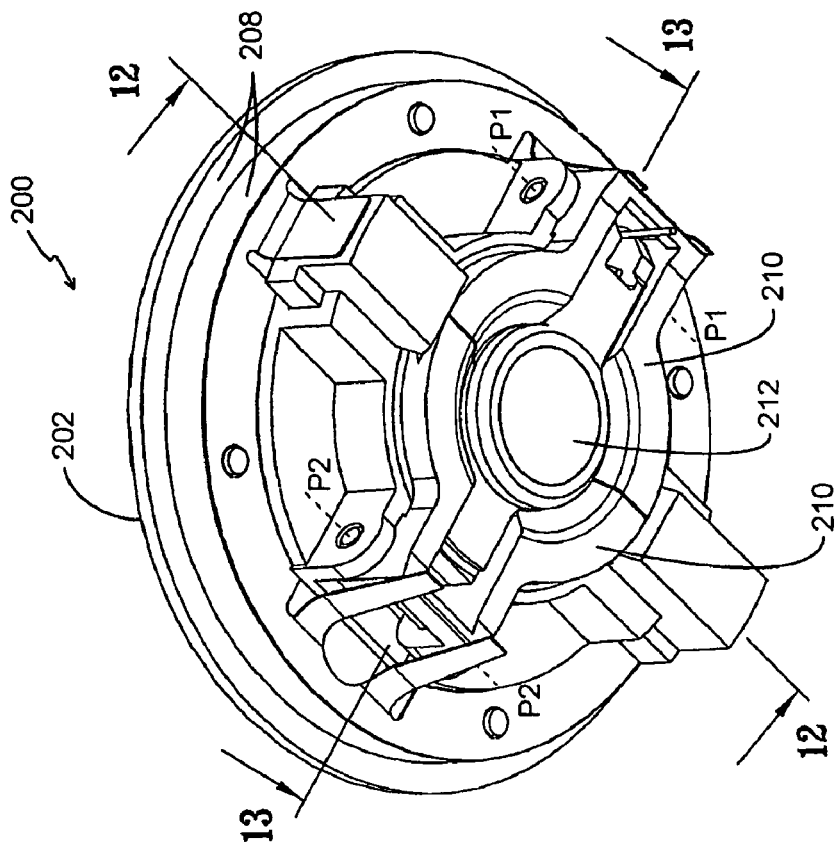
FIG. 10 is a perspective view of a distal side of the seal assembly of FIG. 9.
Figure 9:
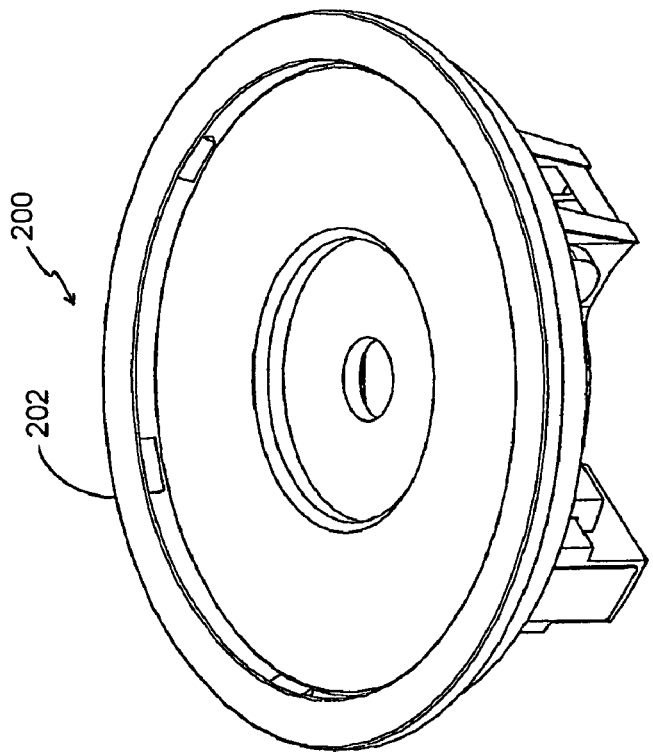
FIG. 9 is a perspective view of a proximal side of a second embodiment of a multi-flapper seal assembly having a bifurcated major flapper in accordance with the present disclosure.

Referring to FIG. 8A, the use of dual flapper seal assembly 100 with broad instrument 50 is described. Broad instrument 50 first encounters septum seal 192 and forms a fluid-tight interface therewith in much the same manner as narrow instrument 40 as described above. As broad instrument 50 travels distally past septum seal 192, however, broad instrument 50 next encounters dimple 168 in elastomeric liner 152. The dimple 168 is pressed against the curved shape of rounded disengagement head 174. As broad instrument 50 moves distally, lock member 172 is urged against the bias of compression spring 180, thereby disengaging catch 176 from notch 178. This disengagement frees major flapper 110 to pivot from its first position to its second position against the bias of torsion spring 130 (transmitted to major flapper 110 through minor flapper 112 and elastomeric plug 140) as it is encountered by broad instrument 50. Minor flapper 112 is caused to pivot along with major flapper 110. With the major flapper 110 open to its second position, the seal through the passageway 28 depends on the interface between the septum seal 192 and the shaft of instrument 50 while broad instrument 50 is in use. When broad instrument 50 is withdrawn in a proximal direction, major flapper 110 is returned to its first position and normally closed biased condition before the seal about the instrument shaft is compromised. In this way a seal across the passageway 28 may be maintained at all times, i.e. before, during and after insertion, use and withdrawal of instrument 50. FIG. 8B depicts dual flapper seal assembly 100 with an open major flapper 110 revealing the major opening 164 through body 102.

Any standard or non standard instrument shaft sizes may be accommodated by such a dual-flapper seal assembly 100. Narrow instrument 40 may have a shaft diameter of about 5 mm to about 18 mm, for example. Broad instrument 50 may have a shaft diameter from about 10 mm to about 18 mm. As used herein, a narrow instrument is any instrument having a diameter smaller than the minor opening 158 that may be accommodated by the opening of the secondary valve, and a broad instrument is any instrument having a diameter larger than the minor opening 158.

Referring now to FIGS. 9 through 15C, a second embodiment of the disclosure includes an embedded valve system with a bifurcated major flapper. Bifurcated flapper seal system 200 generally includes a body 202 having mounting surfaces 208 to permit a fluid tight interface with a housing, such as housing 30 described above. Body 202 also defines a valve mount, which may also be formed integrally with a housing, portal member or other component as described above. Mounting bifurcated flapper seal system 200 to a housing 30 permits bifurcated flapper seal system 200 to seal a passageway 28 through a cannula 20 as described above. A primary valve here includes two major flapper half segments 210 that each abuts a surface such that together they may form a fluid-tight interface with body 102 when primary valve is in its first position. Major flapper half segments 210 may be identical parts oriented oppositely. A secondary valve includes minor flapper 212, which abuts a portion of each of the major flapper half segments 210 to form fluid-tight interface therewith when secondary valve is in its initial position. Minor flapper 212 and one of the major flapper half segments 210 are pivotally mounted on an axis "P1," which is transverse to the longitudinal axis of the cannula 20. The other major flapper half segment 210 is pivotally mounted on an axis "P2" also transverse to the longitudinal axis of cannula 20. Together, the primary valve, including the pair of major flapper half segments 210, and the secondary valve, including minor flapper 212, serve to seal passageway 28 in the absence of an instrument. Components of the primary valve may open to a second position to permit passage of broad instrument and secondary valve may open to an actuated position to permit passage of a narrow instrument as described in greater detail below.

Figure 11:
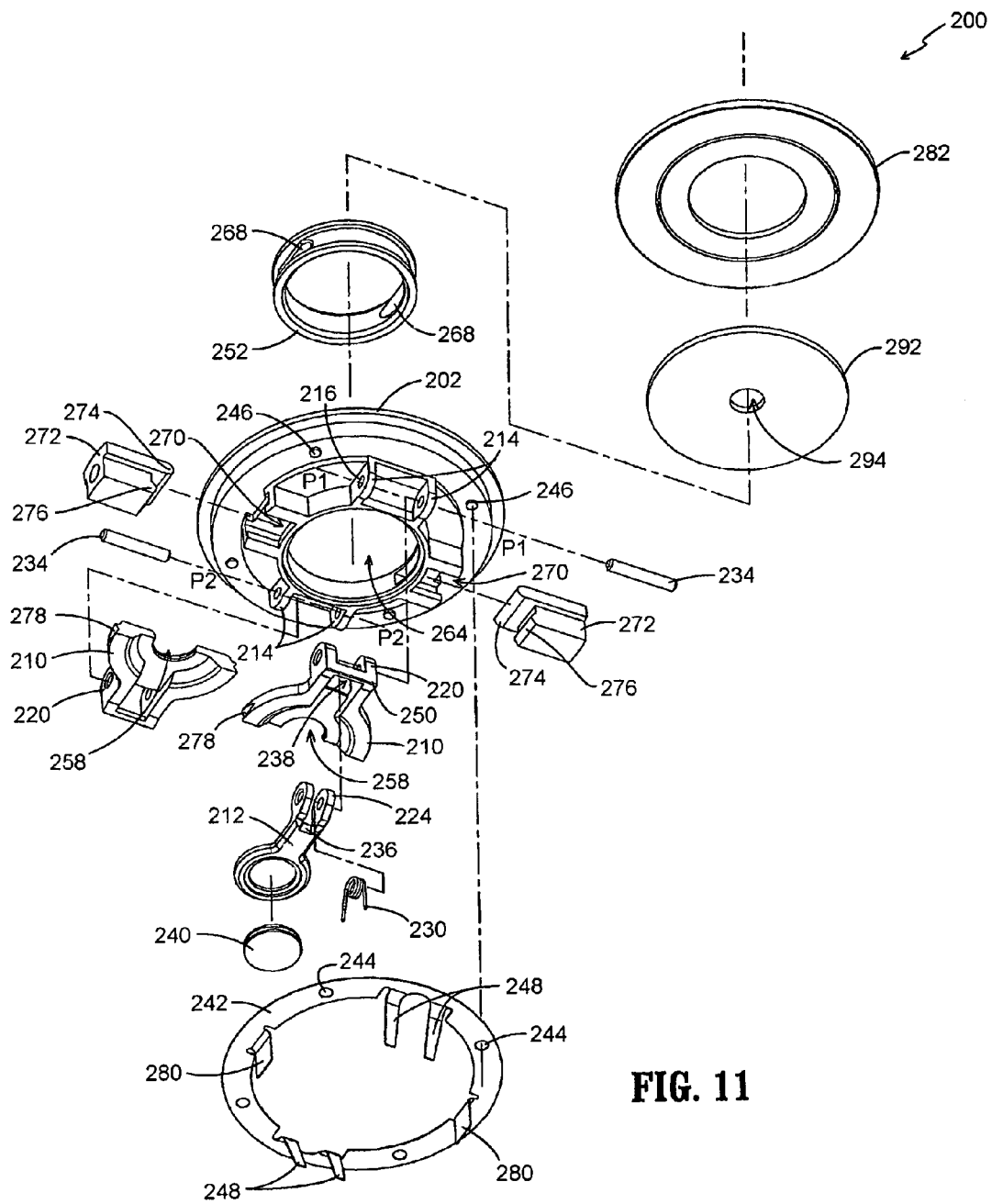
FIG. 11 is perspective view with parts separated of the seal assembly of FIG. 9.

Referring now to FIG. 11, bifurcated flapper seal system 200 includes a body 202 having two pairs of hanging body brackets 214. Each pair of body brackets includes a pair of bores 216 that define one of the pivot axes "P1" and "P2." Body brackets 214 are spaced to receive major brackets 220 extending proximally from major bracket half segments 210. Likewise, major brackets 220 are spaced to receive minor brackets 224 extending proximally from minor flapper 212. Minor brackets 224 are spaced to receive torsion spring 230. A pivot pin 234 may be press fit into bores 216 to secure a major flapper half segment 210, minor flapper 212, and torsion spring 230 to body 202 along axis "P1" while permitting major flapper half segment 210, minor flapper 212, and torsion spring 230 to pivot about axis "P1." An additional pivot pin 234 may be press fit into bores 216 to secure the other major flapper half segment 210 to body 202 while permitting the major flapper half segment 210 to pivot about axis "P2."

Torsion spring 230 exerts pressure against surface 236 on minor flapper 212 and surface 238 on major flapper half segment 210. This arrangement is differentiated from the arrangement of torsion spring 130 (FIG. 5) of seal assembly 100 which exerts pressure on body 102. In this embodiment, because torsion spring 230 is positioned to exert pressure on one of the major flapper half sections 210, the bias is not transmitted through this section 210. Rather torsion spring 230 serves as a biasing member to bias minor flapper 212 to a closed condition with respect to the major flapper half segment 210 mounted pivotally about axis "P1." When both major flapper half sections 210 are in a closed configuration, torsion spring 230 may compress elastomeric plug 240 against both major flapper half sections 210 to form a minor flapper seal. An independent biasing member may be provided for each major flapper half section 210 by spring ring 242.

Spring ring 242 includes an array of holes 244 that correspond to an array of alignment protrusions 246 on body 202 to facilitate attachment of the spring ring 242 to body 202. Spring ring 242 includes two pairs of biasing fingers 248 arranged oppositely such that each pair of biasing fingers 248 may contact a surface 250 on major flapper half segments 210. Biasing fingers 248 tend to bias the major flapper half segments 210 to a closed condition where they may compress a portion of elastomeric liner 252 to create a major flapper seal.

Elastomeric liner 252 is captured within body 202 and remains stationary within body 202. Elastomeric liner 252 includes a pair of oppositely positioned, reduced thickness dimples 268, each aligned with a lateral opening 270 through body 202. Each lateral opening 270 slidingly accepts a lock member 272 such that a rounded disengagement head 274 may protrude against the corresponding dimple 268. Each lock member 272 includes a catch 276 that interfaces with a notch 278 formed in major flapper half segments 210. Biasing tabs 280 are positioned on spring ring 242 such that both lock members 272 are biased radially inward (see, e.g. FIG. 6A).

At the proximal end of bifurcated flapper seal system 200, a cover plate 282 secures septum seal 292 to body 202. Cover plate 282 and septum seal 292 having orifice 294 may function identically as cover plate 182 and septum seal 192 described above with reference to FIG. 5.

Referring now to FIGS. 12 and 13, bifurcated flapper seal assembly 200 is depicted in place within housing 30 in a normally biased condition. As best seen in FIG. 12, lock members 272 are biased inwardly by biasing tabs 280. In this configuration, the catch 276 of each lock member 272 is engaged with the notch 278 formed in the major flapper half segments 210, thus preventing major flapper half segments from moving to an open second position. As best seen in FIG. 13, major flapper half segments 210 are biased to a closed first position by biasing fingers 248 and minor flapper 212 is biased to a closed initial position by torsion spring 230. When in this normally biased configuration, passageway 28 is sealed by fluid tight interfaces formed by the closure biases imparted on major flapper half segments 21 and on minor flapper 212.

Figure 14B:
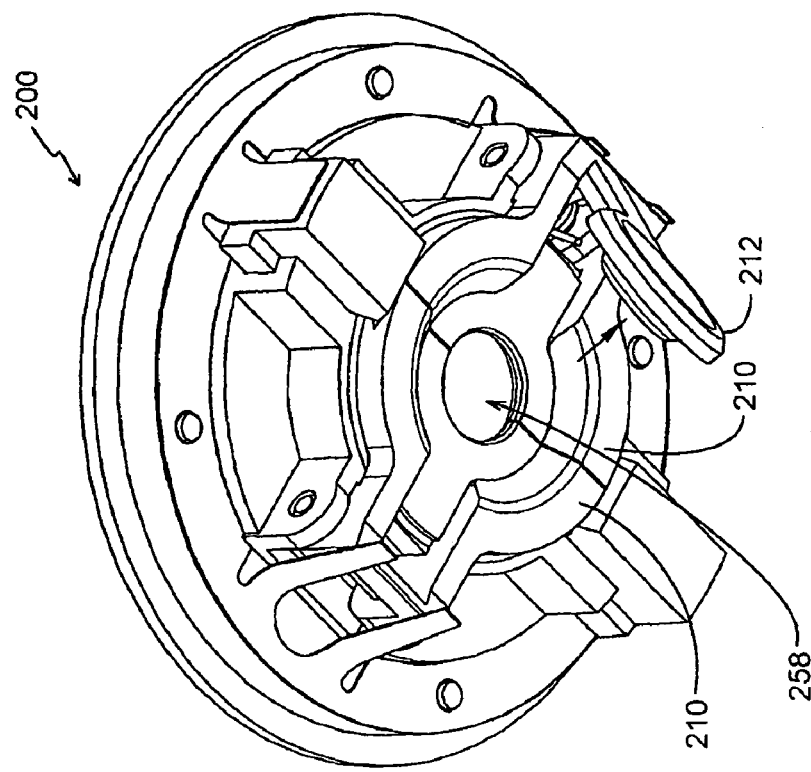
FIG. 14B is a perspective view of a distal side of the seal assembly of FIG. 9 depicting the minor valve in an open configuration.
Figure 14A:
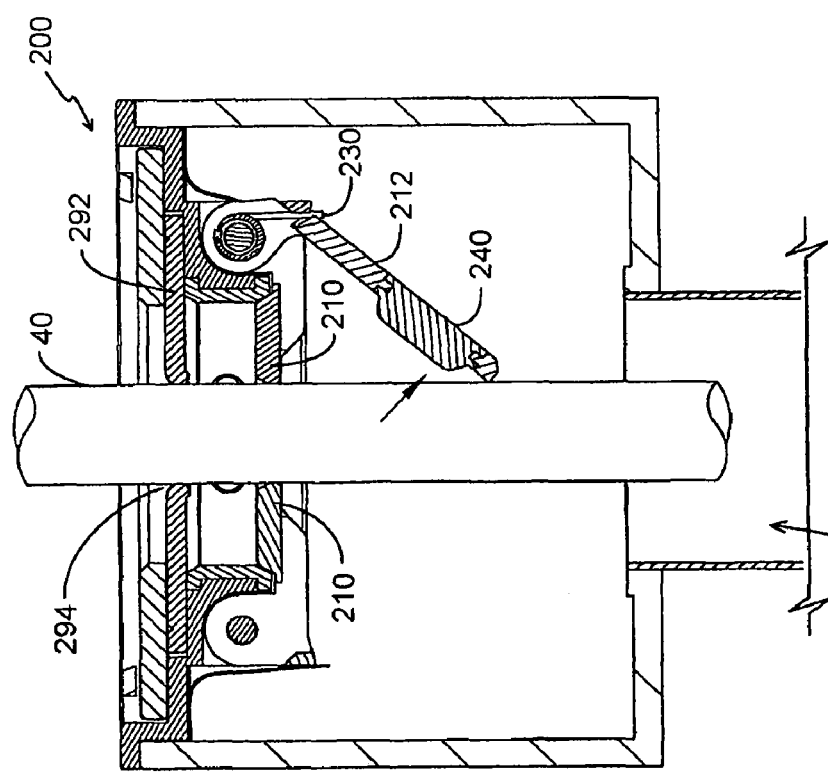
FIG. 14A is a view similar to FIG. 13 depicting a narrow instrument introduced into the proximal end of the portal apparatus.

Referring to FIG. 14A, the use of bifurcated flapper seal assembly 200 with narrow instrument 40 is substantially similar to the use of dual flapper seal assembly 100 with narrow instrument 40 described with reference to FIG. 7A. Narrow instrument 40 first encounters septum seal 292 as it enters seal assembly 200 from a proximal side moving in a distal direction. To accommodate the shaft of narrow instrument 40, septum seal 292 deforms to expand central orifice 294. This deformation creates a fluid-tight interface about the shaft of instrument 40. As it travels distally past septum seal 292, narrow instrument 40 next encounters elastomeric plug 240 and tends to act against the bias of torsion spring 230 to open minor flapper 212 to its actuated position as shown. Any incidental contact with major flapper half segments 210 will not tend to open major flapper half segments 210 due to the engagement of the catches 276 of lock members 272 with the notches 278 formed on major flapper half segments 210 (see FIG. 12). Because major flapper half segments 210 remain closed in a first position, they may assist in centering narrow instrument 40 within the passageway 28.

With the minor flapper 212 open to its actuated position, the seal through the passageway 28 depends on the interface between the septum seal 292 and the shaft of instrument 40 while narrow instrument 40 is in use. When narrow instrument 40 is withdrawn in a proximal direction, minor flapper 212 is returned to its initial position and normally biased closed condition before the seal about the instrument shaft is compromised. In this way, a seal across the passageway 28 may be maintained at all times, i.e. before, during and after insertion, use and withdrawal of instrument 40. FIG. 14B depicts bifurcated flapper seal assembly 200 with minor flapper 212 open to its actuated position revealing minor opening 258.

Referring to FIGS. 15A and 15B, the use of bifurcated flapper seal assembly 200 with broad instrument 50 is described. Broad instrument 50 first encounters septum seal 292 and forms a fluid-tight interface therewith in much the same manner as narrow instrument 40 as described above. As seen in FIG. 15A, as broad instrument 50 travels distally past septum seal 292, broad instrument 50 next encounters the pair of dimples 268 in elastomeric liner 252. The dimples 268 are pressed against rounded disengagement heads 272 such that lock members 272 are urged against the bias of biasing tabs 280, thereby disengaging catches 276 from notches 278. As seen in FIG. 15B, this disengagement frees major flapper half segments 210 to pivot against the bias of biasing fingers 230 as they are encountered by broad instrument 50, thus opening the primary valve to its second position. Minor flapper 212 is caused to pivot along with the major flapper half segment 210 to which it is mounted. Because torsion spring 230 is mounted to major flapper half section 210 rather than body 202, the closure bias of each major flapper half section 210 imparted to the shaft of broad instrument 50 may be balanced such that this bias tends to center broad instrument 50 within passageway 28.

Figure 15C:
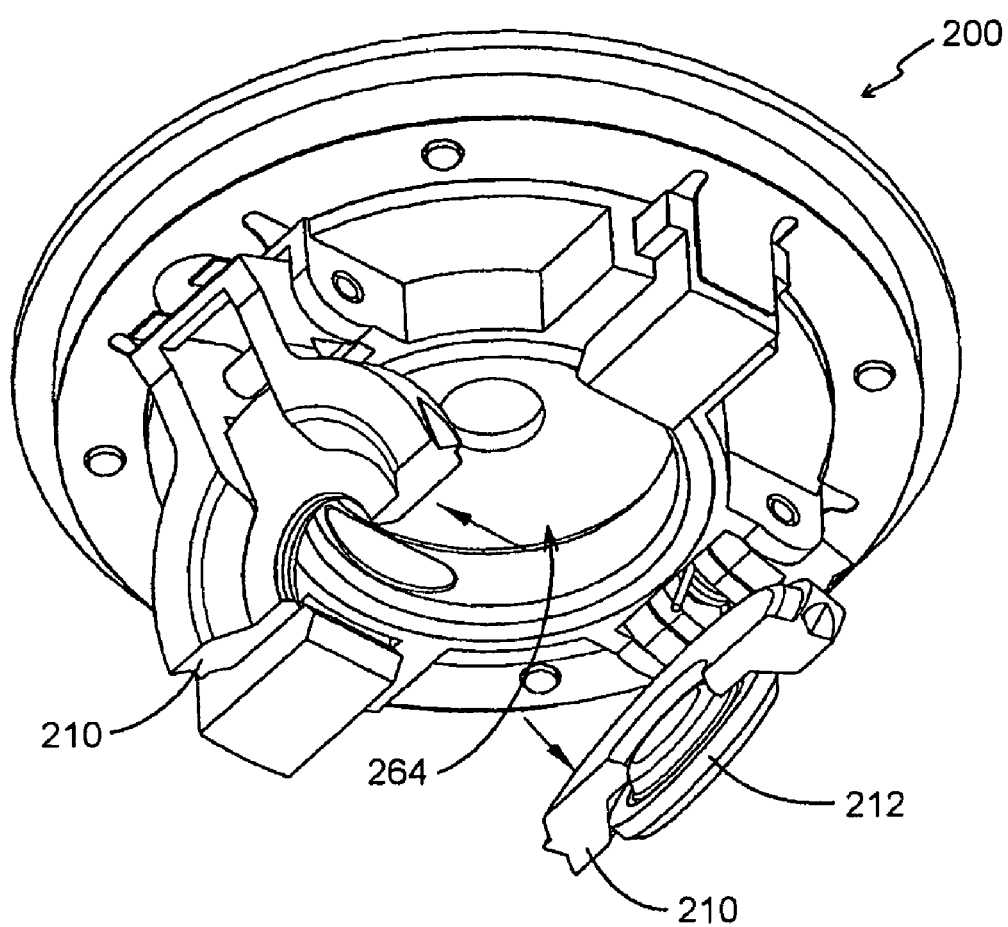
FIG. 15C is a perspective view of a distal side of the seal assembly of FIG. 9 depicting the bifurcated major valve in an open configuration.
Figure 17:
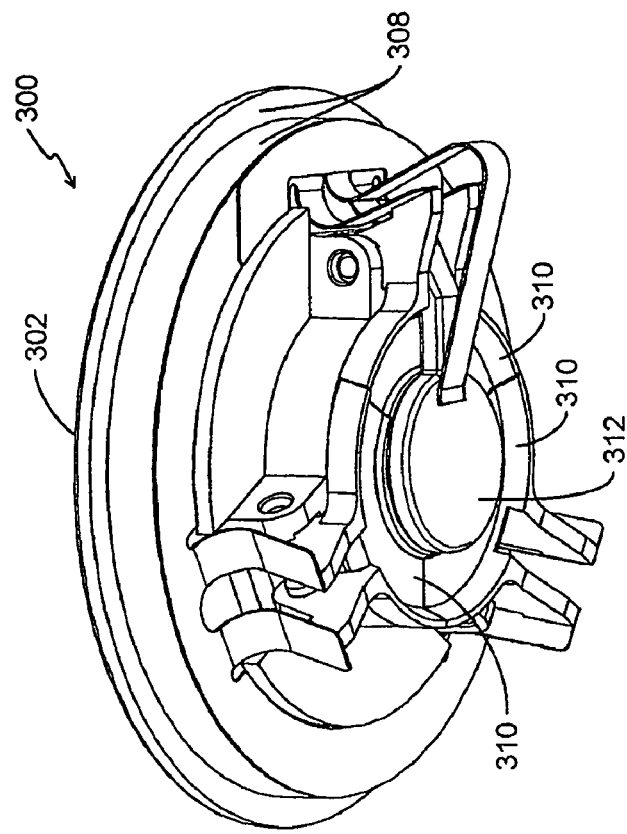
FIG. 17 is a perspective view of a distal side of the seal assembly of FIG. 16.
Figure 16:
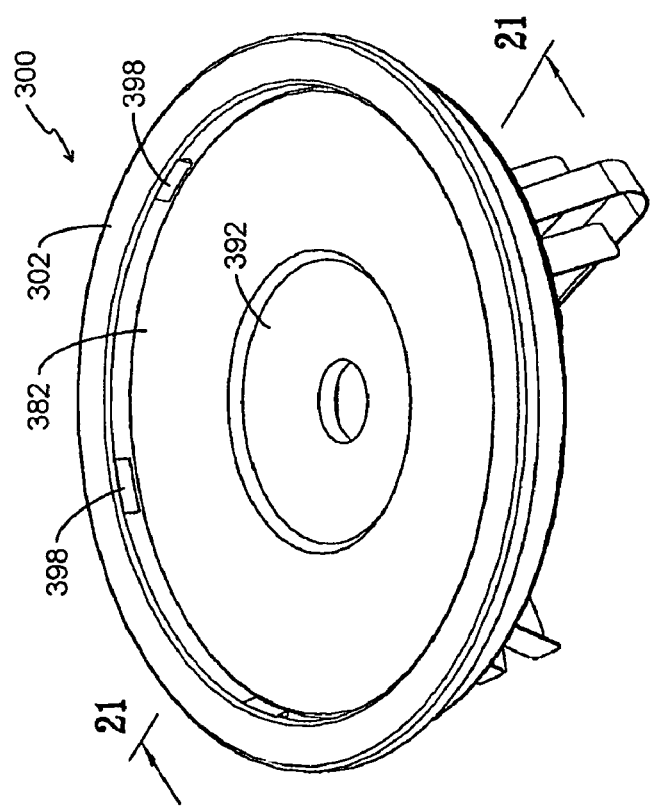
FIG. 16 is a perspective view of a proximal side of a third embodiment of a multi-flapper seal assembly having a radially segmented major flapper in accordance with the present disclosure.

With the major flapper half segments 210 open, the seal through the passageway 28 depends on the interface between the septum seal 292 and the shaft of instrument 50 while broad instrument 50 is in use. When broad instrument 50 is withdrawn in a proximal direction, major flapper half segments 210 are returned to their normally closed biased condition, thus returning the primary valve to is first position, before the seal about the instrument shaft is compromised. In this way a seal across the passageway 28 may be maintained at all times, i.e. before, during and after insertion, use and withdrawal of instrument 50. FIG. 15C depicts bifurcated flapper seal assembly 200 with open major flapper half segments 210 revealing major opening 264.

Referring now to FIGS. 16 through 23B, a third embodiment of the disclosure includes an embedded valve assembly with a trifurcated major flapper. Trifurcated flapper seal system 300 generally includes a body 302 having mounting surfaces 308 to permit a fluid tight interface with a housing, such as housing 30 described above. Again, body 302 also defines a valve mount, which may also be formed integrally with a housing, portal member or other component as described above. Mounting trifurcated flapper seal system 300 to a housing 30 permits trifurcated flapper seal system 300 to seal a passageway 28 through a cannula 20 as described above. A primary valve here has a first position wherein three major flapper third segments 310 that each abuts a surface such that together they may form a fluid-tight interface with body 302. Major flapper third segments 310 may be identical parts oriented cooperatively around body 302. A secondary valve includes minor flapper 312, which abuts a portion of the major flapper third segments 310 to form fluid-tight interface therewith. Minor flapper 312 and one of the major flapper third segments 310 are pivotally mounted on an axis "P3" transverse to the longitudinal axis of the cannula 20. The other major flapper third segments 310 are pivotally mounted on an axes "P4" and "P5," each also transverse to the longitudinal axis of cannula 20. Together, the primary valve, including the set of major flapper third segments 310, in a first position and the secondary valve, including minor flapper 312, in an initial position serve to seal passageway 28 in the absence of an instrument. The primary valve may open to a second position to permit passage of a broad instrument and the secondary valve may open to an actuated position to permit passage of a narrow instrument as described in greater detail below.

Figure 18:
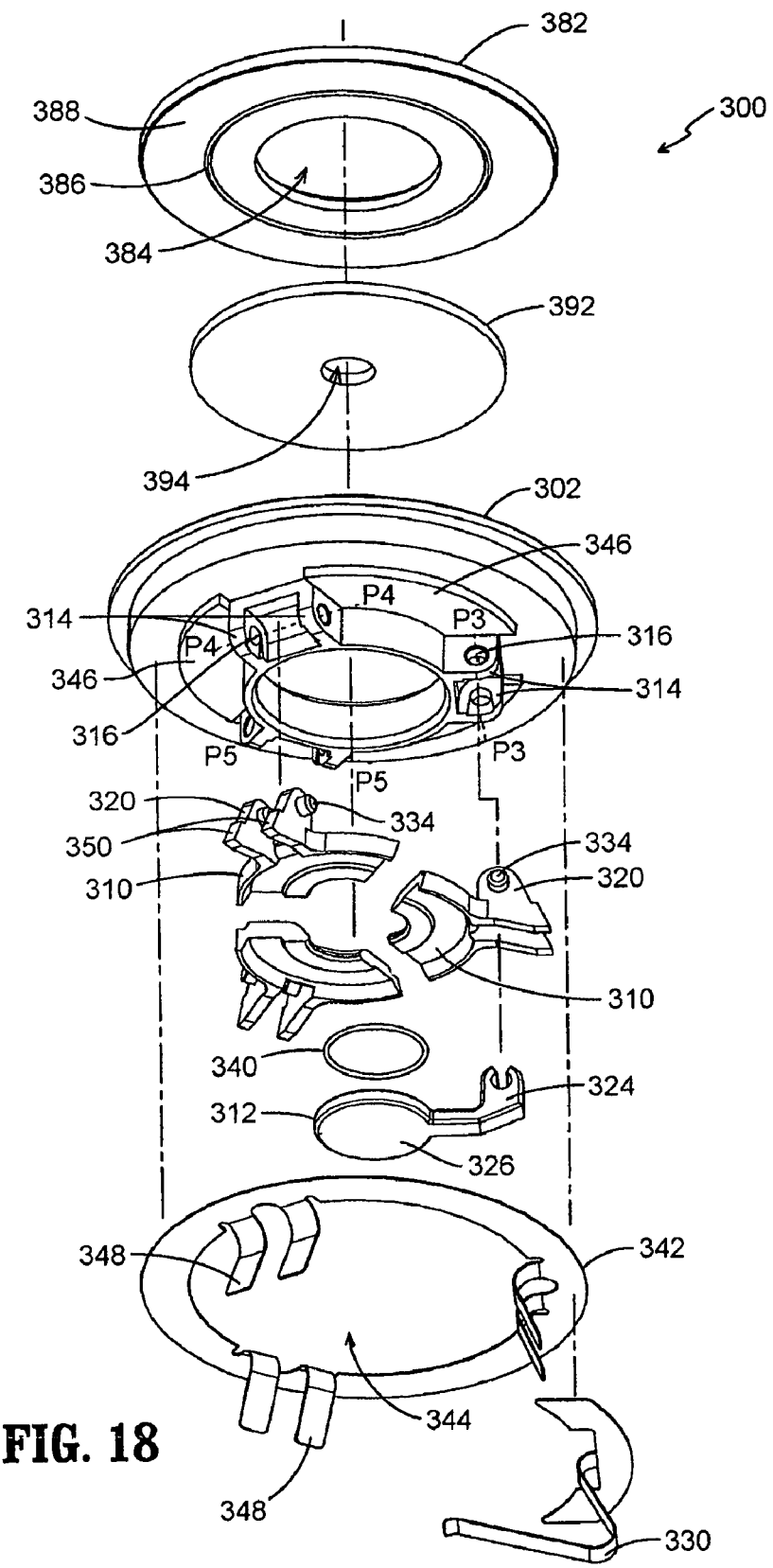
FIG. 18 is perspective view with parts separated of the seal assembly of FIG. 16.

Referring now to FIG. 18, trifurcated flapper seal assembly 300 includes a body 302 having three pairs of hanging body brackets 314. Each pair of body brackets 314 includes a pair of bores 316 that define one of the pivot axes "P3," "P4" and "P5." Body brackets 314 include tapered guide surfaces and are spaced to receive major brackets 320 extending proximally from major bracket third segments 310. Likewise, major brackets 320 are spaced to receive minor bracket 324 extending proximally from minor flapper 312. Minor bracket 324 does not accommodate a torsion spring like the minor brackets 124 and 224 discussed with reference to FIGS. 5 and 11 above. In this embodiment, the torsion spring is replaced with leaf spring 330. Pivot bosses 334 extend laterally from both sides of major brackets 320. Exterior pivot bosses 334 may be snap fit into bores 316 to pivotally secure a major flapper third segments 310 to body 302. As best seen in FIGS. 19 and 20, minor flapper 312 may be snap fit onto the interior pivot bosses 334 of one of the major flapper third segments 310 to pivotally secure minor flapper 312 thereto. The major flapper third segment 310 attached to minor flapper 312 may be snap fit to body 302 in the same manner as major flapper third segments 310 not attached to minor flapper 312.

Leaf spring 330 exerts pressure against surface 336 on minor flapper 312. Leaf spring 330 biases minor flapper 312 to a closed condition and may compress elastomeric o-ring 340 against all three major flapper third segments 310 to form a minor flapper seal. Leaf spring 330 thus imparts a bias on each of the major flapper third segments 310 when minor flapper 312 is in a closed condition. An additional bias may be imposed on third segments 310, even when minor flapper 312 is in an open condition, by spring ring 342.

Spring ring 342 includes an open central portion 344 that fits around an array of protrusions 346 on body 302 to facilitate attachment of the spring ring 342 to body 302. Spring ring 342 may be affixed to body 302 by a friction fit or with an appropriate adhesive. Spring ring 342 includes three pairs of biasing fingers 348 arranged such that each pair of biasing fingers 348 may contact a surface 350 on major flapper third segments 310. Biasing fingers 348 tend to bias the major flapper third segments 310 to a closed condition where they may contact a portion of body 302 to create a major flapper seal.

This embodiment does not include an elastomeric liner or a lock member as described in other embodiments with reference to FIGS. 5 and 11. At the proximal end of trifurcated flapper seal system 300, a cover plate 382 includes a central opening 384 and an annular ridge 386 protruding from a distal face 388. Annular ridge 386 is tapered or pointed in cross section such that it may dig into and deform a portion of septum seal 392 to secure its relative position against distal face 388. Septum seal 392 is a relatively flat member formed from a low durometer polymer making it particularly adaptable and deformable. Extending through a central portion of septum seal 392 is an orifice 394, which is capable of expanding to accommodate instruments of various sizes. Septum seal 392 is held in place between body 302 and cover plate 382 by a radial array of flaps 398 (best seen in FIG. 16) protruding inwardly from body 302.

Referring now to FIG. 21, trifurcated flapper seal assembly 300 is depicted in place within housing 30 in a normally biased condition. Major flapper third segments 310 are biased to a closed position by biasing fingers 348 such that the primary valve is in its first position. An additional bias is provided through minor flapper 312, which is itself biased to a closed initial position by leaf spring 330. When trifurcated flapper seal assembly 300 is in this normally biased configuration, passageway 28 is sealed by fluid tight interfaces formed by the bias imparted on the set of major flapper third segments 310, and minor flapper 312.

Referring to FIG. 22A, the use of bifurcated flapper seal assembly 300 with narrow instrument 40 is described. Narrow instrument 40 first encounters septum seal 392 as it enters seal assembly 300 from a proximal side moving in a distal direction. To accommodate the shaft of narrow instrument 40, septum seal 392 deforms to expand central orifice 394. This deformation creates a fluid-tight interface about the shaft of instrument 40. As it travels distally past septum seal 392, narrow instrument 40 next encounters minor flapper 312 and it tends to act against the bias of leaf spring 330 to open minor flapper 312, moving the secondary valve to its actuated position as shown. Any incidental contact with major flapper third segments 310 may tend to open major flapper third segments 310 against the bias imparted by biasing fingers 348. However, once instrument 40 is through the opening, the bias of the major flapper third segments 310 tends to centralize instrument 40 within passageway 28. With the minor flapper 312 open to an actuated position, the seal through the passageway 28 depends on the interface between the septum seal 392 and the shaft of instrument 40 while narrow instrument 40 is in use. When narrow instrument 40 is withdrawn in a proximal direction, minor flapper 312 is returned to its initial position and normally closed biased condition before the seal about the instrument shaft is compromised. In this way, a seal across the passageway 28 may be maintained at all times, i.e. before, during and after insertion, use and withdrawal of instrument 40. FIG. 22B depicts trifurcated flapper seal assembly 300 with a minor flapper 312 open to its actuated position revealing opening 358 formed by the combination of major flapper third segments 310.

Referring to FIG. 23A, the use of trifurcated flapper seal assembly 300 with broad instrument 50 is described. Broad instrument 50 first encounters septum seal 392 and forms a fluid-tight interface therewith in much the same manner as narrow instrument 40 as described above. As broad instrument 50 travels distally past septum seal 392 however, broad instrument 50 next encounters the set of major flapper third segments 310. Each major flapper third segment pivots about its corresponding axis as it is displaced to its open condition moving the primary valve to its second position as shown. Minor flapper 312 is also displaced as a consequence of the introduction of broad instrument 50. With the major flapper third segments 310 open, the seal through the passageway 28 depends on the interface between the septum seal 382 and the shaft of instrument 50 while broad instrument 50 is in use. When broad instrument 50 is withdrawn in a proximal direction, major flapper third segments 310 are returned to their normally closed biased condition, thus returning the primary valve to its first position, before the seal about the instrument shaft is compromised. In this way a seal across the passageway 28 may be maintained at all times, i.e. before, during and after insertion, use and withdrawal of instrument 50. FIG. 23B depicts trifurcated flapper seal assembly 300 with open major flapper third segments 310 revealing an opening 364 through body 302.

Although the foregoing disclosure has been described in some detail by way of illustration and example, for purposes of clarity or understanding, it will be obvious that certain changes and modifications may be practiced within the scope of the appended claims.

What is claimed is:

1. A surgical portal apparatus for permitting access to a tissue site, which comprises:

a portal member dimensioned for positioning within body tissue and defining a longitudinal axis, the portal member having a longitudinal passageway therethrough providing access to a tissue site, the portal member having a valve mount defining a major opening in communication with the longitudinal passageway;

a primary valve mounted to the portal member, the primary valve adapted to move between a first position to substantially seal the major opening of the valve mount, and a second position displaced from the major opening to permit passage of a relatively broad surgical instrument through the major opening, the primary valve defining a minor opening dimensioned to receive a relatively narrow instrument;

a secondary valve mounted to the portal member, the secondary valve adapted to move relative to the primary valve between an initial position substantially sealing the minor opening of the primary valve, and an actuated position displaced from the minor opening to permit passage of the narrow instrument and a lock member adapted to prevent the primary valve from opening upon introduction of the narrow instrument, the lock member including a disengagement surface biased radially inward for engaging the broad instrument such that the lock member is displaced against its bias to permit the primary valve to open to permit passage of the broad instrument.

2. The surgical portal apparatus according to claim 1, further comprising a housing coupled to a proximal end of the portal member, the valve mount coupled to the housing.

3. The surgical portal apparatus according to claim 1, further comprising a septum seal disposed proximally with respect to the primary valve, the septum seal adapted for engaging an instrument and forming a seal therewith.

4. The surgical portal apparatus according to claim 1, wherein the primary valve and the secondary valve are normally biased to their respective first and initial positions such that a fluid-tight seal is maintained across the passageway in the absence of an instrument.

5. The surgical portal apparatus according to claim 1, wherein at least one of the primary valve and the secondary valve is adapted for pivotal movement about an axis transverse to the longitudinal axis.

6. The surgical portal apparatus according to claim 5, wherein the major valve is radially segmented such that a plurality of segments are disposed about the major opening, each segment adapted to pivot about an independent axis transverse to a longitudinal axis of the passageway.

7. The surgical portal apparatus according to claim 6, wherein the major valve is bifurcated to include two radial segments.

8. The surgical portal apparatus according to claim 6, wherein the major valve is trifurcated to include three radial segments.

9. A cannula seal comprising:
a valve mount for mounting the cannula seal across a passageway through a cannula defining a longitudinal axis;
a primary valve for selectively sealing a major opening through the valve mount, the primary valve radially segmented to include a plurality of segments, each segment mounted pivotally about an axis transverse to the longitudinal axis of the cannula and movable to move the primary valve between a first position and a second position, the plurality of segments arranged so as to define a minor opening through the primary valve when in the first position;
a secondary valve for selectively sealing the minor opening, the secondary valve coupled to at least one of the segments such that the secondary valve is displaced when the primary valve is moved between the first position and the second position; and
a lock member adapted to prevent the plurality of segments from pivoting upon introduction of the narrow instrument, the lock member including a disengagement surface biased radially inward for engaging the broad instrument such that the lock member is displaced against its bias to permit the plurality of segments to pivot to permit passage of the broad instrument.

10. The cannula seal according to claim 9, further comprising a septum seal disposed proximally with respect to the primary valve, the septum seal adapted for engaging an instrument and forming a seal therewith.

11. The cannula seal according to claim 9, wherein the lock member includes a catch that interfaces with at least two segments of the plurality of segments to prevent the plurality of segments from opening.

12. The cannula seal according to claim 9, wherein the cannula seal includes a pair of lock members, the pair of lock members including opposing disengagement surfaces biased radially inward.

13. The cannula seal according to claim 9, wherein the secondary valve is mounted pivotally about the axis about which at least one of the segments is pivotally mounted.

14. The cannula seal according to claim 13, wherein the secondary valve is biased by a biasing member to an initial position to seal the minor opening.

15. A surgical portal apparatus for permitting access to a tissue site, which comprises:
a portal member dimensioned for positioning within body tissue and defining a longitudinal axis, the portal member having a longitudinal passageway therethrough providing access to a tissue site, the portal member having a valve mount defining a major opening in communication with the longitudinal passageway;
a primary valve mounted to the portal member, the primary valve adapted to move between a first position to substantially seal the major opening of the valve mount, and a second position displaced from the major opening, the primary valve defining a minor opening, the minor opening having an internal dimension less than a corresponding internal dimension of the major opening of the valve mount;
a secondary valve mounted to the portal member, the secondary valve adapted to move relative to the primary valve between an initial position substantially sealing the minor opening of the primary valve, and an actuated position displaced from the minor opening; and
a lock member adapted to prevent the primary valve from opening upon introduction of the narrow instrument, the lock member including a disengagement surface biased radially inward for engaging the broad instrument such that the lock member is displaced against its bias to permit the primary valve to open to permit passage of the broad instrument.

* * * * *